US012758411B2

(12) United States Patent
Fazulyanov et al.

(10) Patent No.: US 12,758,411 B2
(45) Date of Patent: Oct. 13, 2026

(54) OFFLOADING DEVICE

(71) Applicants: Ildar Fazulyanov, Culver City, CA (US); Joshua Vanderpool, Milwaukie, OR (US)

(72) Inventors: Ildar Fazulyanov, Culver City, CA (US); Joshua Vanderpool, Milwaukie, OR (US)

(73) Assignee: Eazistep LLC, Provo, UT (US)

( * ) Notice: Subject to any disclaimer, the term of this patent is extended or adjusted under 35 U.S.C. 154(b) by 71 days.

(21) Appl. No.: 18/423,325

(22) Filed: Jan. 26, 2024

(65) Prior Publication Data

US 2024/0252338 A1 Aug. 1, 2024

Related U.S. Application Data

(60) Provisional application No. 63/441,783, filed on Jan. 28, 2023.

(51) Int. Cl.
*A61F 5/01* (2006.01)
*A61F 5/30* (2006.01)

(52) U.S. Cl.
CPC .............. *A61F 5/0111* (2013.01); *A61F 5/30* (2013.01); *A61F 2005/0137* (2013.01)

(58) Field of Classification Search
CPC ........ A61F 5/0111; A61F 5/0127; A61F 5/30; A61F 2005/0137; A61F 5/0123; A61F 5/0104; A61F 5/0195; A61F 5/0102; A61F 5/01; A61F 5/0125; A61F 2005/0172; A61F 2005/0174
USPC ........................................................... 602/16
See application file for complete search history.

(56) References Cited

U.S. PATENT DOCUMENTS

| | | | | |
|---|---|---|---|---|
| 5,209,722 A * | 5/1993 | Miklaus | ................ | A61F 5/0127 602/27 |
| 5,971,946 A | 10/1999 | Quinn et al. | | |
| 2005/0274046 A1* | 12/2005 | Schwartz | ............. | A61F 5/0127 36/110 |
| 2022/0054291 A1 | 2/2022 | Huber | | |

FOREIGN PATENT DOCUMENTS

FR 2840525 A1 * 12/2003 ............ A61F 5/0111

OTHER PUBLICATIONS

Translation of FR-2840525-A1 (Year: 2003).*

* cited by examiner

*Primary Examiner* — Daniel A Miller
(74) *Attorney, Agent, or Firm* — Willie Jacques; Emanus LLC

(57) ABSTRACT

An offloading device for supporting an ankle joint of a user, includes a foot locating member configured to locate therewithin a foot of the user. Furthermore, one or more bracing members are pivotably coupled to the foot locating member. Furthermore, one or more liner pads are provided on inner surfaces of the one or more bracing members. Also included is a fastening arrangement configured to fasten the one or more bracing members to a portion of a lower leg that is located above the ankle joint. The one or more liner pads are made from a deformable material coated with a contact material, static coefficient of friction of the contact material ranging from 0.4 to 1.0, and kinetic coefficient of friction ranging from 0.3 to 0.8. The foot locating member may be embodied as a basal locating member coupled with left-side and right-side arm members or as a wearable shoe.

16 Claims, 25 Drawing Sheets

900

OFFLOADING DEVICE

TECHNICAL FIELD

The present invention relates generally to medical devices. More specifically, the present invention relates to orthotic devices for supporting the ankle joints of people suffering from arthritis, osteoarthritis, diabetes, ankle sprains, and other deformities.

BACKGROUND ART

Plantar flexion and dorsi flexion are two main movements of ankle joints (See FIG. 1A). They are essential for activities such as walking, running, jumping, etc. During plantar flexion, toes are pointed downwards and are applying force against the ground. Plantar flexion involves the contraction of calf muscles located at the back of the lower leg of a person (See FIG. 1B). On the contrary, in dorsi flexion the toes are pointed upwards towards the shin. Dorsi flexion involves the contraction of muscles in the front portion of the person, such as the tibialis anterior (See FIG. 1B). Both plantar flexion and dorsi flexion are important for maintaining good ankle mobility and preventing injuries. Having a good range of motion in both directions can help you perform everyday activities more easily and efficiently.

However, in patients suffering from ailments that affect ankle joints, such as arthritis, osteoarthritis, ankle sprains, and other deformities, both plantar flexion and dorsi flexion are restricted and often painful. The restriction may be caused due to pain and stiffness caused by inflammation and muscle weakness, causing cascading symptoms such as decreased mobility, increased pain, and degradation in overall quality of life. According to a study published by the National Library of Medicine, National Institute of Health (NIH), United States of America, it is estimated that ankle osteoarthritis alone affects up to 1% of the entire adult population in the United States. Moreover, ankle osteoarthritis can also cause pain when a normal load is put on the ankle, regardless of ankle flexion.

One common treatment for such ailments is a restrictive brace to prevent ankle flexion. These devices eliminate pain for some, but also eliminate ankle mobility and do not reduce the load on the ankle. This load is a primary contributor to pain. The loss of ankle mobility may also be counterproductive to the treatment of arthritis, as movement in a joint with some pressure is what lubricates and maintains cartilage in that joint. Offloading devices for ankle joints allows a patient to have relatively greater mobility. Current offloading devices aim to attain certain key objectives such as pressure redistribution, improved alignment and gait, and reduced muscle strain.

Many ankle braces to be used as offloading devices have been suggested in the art, but fail to promote function while reducing pain. For example, many offloading ankle braces restrict plantar flexion leading to increased muscle atrophy. Other offloading devices offload via only a compressive force with a common coefficient of friction such as that between a cloth and the skin, which is not sufficient to offload enough weight to reduce pain and symptoms. The magnitude of offloading is important to the reduction of pain. Several other braces offload by applying a load exclusively at the patellar tendon (See FIG. 1C). Moreover, currently available devices are large and bulky and therefore cumbersome to carry around, discouraging sufferers of the previously mentioned conditions from using the devices.

Therefore, there is a need in the art for an offloading device that does not suffer from the aforementioned deficiencies.

OBJECTS OF THE INVENTION

Some of the objects of the present invention are as follows:

An object of the present invention is to provide an offloading device that allows for a full range of motion in dorsi and plantar flexion, successfully redistributes weight above the ankle, and does so all while inconspicuously while fitting inside a wearable shoe or while being embodied as a wearable shoe itself.

Another object of the present invention is to provide an offloading device that allows reactionary force being applied to an ankle joint by the ground to be offloaded to portions of the lower leg of a user, which lie above the ankle joints.

Another object of the invention is to provide an offloading device that not only reduces or eliminates reactionary forces acting on the ankle joint but also provides cushion or clearance to the heel and/or midfoot which is desirable for patients suffering from diabetic ulcers and other foot injuries.

Another object of the present invention is to provide an offloading device that includes a rigid support member that makes contact with the ground, and bracing members connected to the rigid support member that transfer the reactionary forces being applied to the rigid support member to the portions of the lower leg that lie above the ankle joint.

Another object of the present invention is to provide an offloading device that includes an insole member that cushions at least the posterior portion of the foot of the user thereby allowing muscles and/or outer skin in the lower leg, and above the ankle joint, to stretch while being held firmly by the bracing members.

Another object of the present invention is to provide an offloading device in which the bracing members are provided with inner liners that are deformable and skin-friendly to not cause any adverse effects to blood supply in the lower leg or allergic reactions to the portion of the skin in the lower leg.

Another object of the present invention is to provide an offloading device in which the bracing members may be fastened to the portion of the lower leg above the ankle joint with fastening arrangements such as belts or straps.

Another object of the present invention is to provide an offloading device in which the portion of the offloading device supporting the foot may also be embodied as a wearable shoe.

SUMMARY OF THE INVENTION

According to a first aspect of the present invention, there is provided an offloading device for supporting an ankle joint of a user. The offloading device includes a foot locating member configured to locate therewithin a foot of the user. Furthermore, the offloading device includes one or more bracing members pivotably coupled to the foot locating member on a left side and a right side of the foot locating member, the one or more bracing members configured to grasp a portion of a lower leg that is located above the ankle joint. The offloading device further includes one or more liner pads provided on inner surfaces of the one or more bracing members, wherein the one or more liner pads are configured to make contact with skin of the user. Also, the offloading device includes a fastening arrangement configured to fasten the one or more bracing members to the portion of the lower leg that is located above the ankle joint. Furthermore, the one or more liner pads are made from a deformable material coated with a contact material, static coefficient of friction of the contact material ranging from 0.4 to 1.0, and kinetic coefficient of friction of the contact material ranging from 0.3 to 0.8.

In one embodiment of the invention, the one or more bracing members and the foot locating member form a unitary structure, and the one or more bracing members are pivotably coupled to the foot locating member through flexure hinges at the left side and the right side of the foot locating member.

In one embodiment of the invention, the offloading device further includes an insole member fastened to the foot locating member, the insole member including an insole anterior portion and an insole posterior portion, wherein at least the insole posterior portion is configured to undergo deformation within a predetermined range.

In one embodiment of the invention, the insole member is in contact with and bonded to the foot locating member, along entire length of the foot locating member, the insole member being made from a deformable material.

In one embodiment of the invention, at least the insole posterior portion is suspended from lateral surfaces of the foot locating member.

In one embodiment of the invention, the foot locating member includes a basal locating member made from a rigid material, a left-side arm member, and a right-side arm member, the left-side arm member and the right-side arm member coupled to the basal locating member, on a left and a right side of the basal locating member, respectively.

In one embodiment of the invention, one or more bracing members are pivotably coupled to the foot locating member through first apertures provided in upper portions of the left-side arm member and the right-side member, respectively, the first apertures aligning with second apertures provided in lower portions of the one or more bracing members.

In one embodiment of the invention, the foot locating member is embodied as a wearable shoe.

In one embodiment of the invention, the one or more bracing members are pivotably coupled to the wearable shoe, through first apertures provided in upper portions of a left-side quarter portion and a right-side quarter portion of the wearable shoe, respectively, the first apertures aligning with second apertures provided in lower portions of the one or more bracing members.

In one embodiment of the invention, the offloading device further includes an insole member including an insole anterior portion and an insole posterior portion. Furthermore, the foot locating member is fastened to the insole member along a periphery of the insole member, with a predefined clearance between ground and at least the insole posterior portion.

In one embodiment of the invention, the offloading device further includes an insole member including an insole anterior portion and an insole posterior portion. Furthermore, the foot locating member is fastened to the insole member along a periphery of the insole member, with the insole member being in contact with the ground and made from a deformable material.

In one embodiment of the invention, the fastening arrangement includes a plurality of belts and/or a plurality of straps.

In one embodiment of the invention, the plurality of belts and/or the plurality of straps are provided with one or more a loops and hooks fastening arrangement, a buckle pin and holes fastening arrangement, and a spring-loaded friction buckle fastening arrangement.

According to a second aspect of the present invention, there is provided an offloading device for supporting an ankle joint of a user. The offloading device includes a foot locating member configured to locate therewithin a foot of the user. Furthermore, the offloading device includes one or more bracing members pivotably coupled to the foot locating member on a left side and a right side of the foot locating member, the one or more bracing members configured to grasp a portion of a lower leg that is located above the ankle joint. The offloading device further includes one or more liner pads provided on inner surfaces of the one or more bracing members, wherein the one or more liner pads are configured to make contact with skin of the user. Also, the offloading device includes a fastening arrangement configured to fasten the one or more bracing members to the portion of the leg that is located above the ankle joint. Furthermore, the foot locating member comprises a basal locating member made from a rigid material, a left-side arm member, and a right-side arm member, the left-side arm member and the right-side arm member coupled to the basal locating member, on a left and a right side of the basal locating member, respectively. Also, the one or more liner pads are made from a deformable material coated with a contact material, static coefficient of friction of the contact material ranging from 0.4 to 1.0, and kinetic coefficient of friction of the contact material ranging from 0.3 to 0.8.

In one embodiment of the invention, one or more bracing members are pivotably coupled to the foot locating member through first apertures provided in upper portions of the left-side arm member and the right-side member, respectively, the first apertures aligning with second apertures provided in lower portions of the one or more bracing members.

In one embodiment of the invention, the offloading device further includes an insole member provided above an upper surface of the basal locating member, the insole member including an insole anterior portion and an insole posterior portion, wherein at least the insole posterior portion is configured to undergo deformation within a predetermined range.

In one embodiment of the invention, the insole member is in contact with and bonded to the basal locating member, along entire length of the basal locating member, the insole member being made from a deformable material.

In one embodiment of the invention, at least the insole posterior portion is suspended from the left-side arm member and the right-side arm member.

In one embodiment of the invention, the fastening arrangement includes a plurality of belts and/or a plurality of straps.

According to a third aspect of the present invention, there is provided an offloading device for supporting an ankle joint of a user. The offloading device includes a foot locating member configured to locate therewithin a foot of the user. The offloading device further includes an insole member fastened to the foot locating member, the insole member including an insole anterior portion and an insole posterior portion, wherein at least the insole posterior portion is configured to undergo deformation within a predetermined range. Furthermore, the offloading device includes one or more bracing members pivotably coupled to the foot locating member on a left side and a right side of the foot locating member, the one or more bracing members configured to grasp a portion of a lower leg that is located above the ankle joint. The offloading device also includes a fastening arrangement configured to fasten the one or more bracing members with the portion of the lower leg that is located above the ankle joint. Furthermore, the foot locating member is embodied as a wearable shoe.

In one embodiment of the invention, the foot locating member is fastened to the insole member along a periphery of the insole member, with a predefined clearance between ground and at least the insole posterior portion.

In one embodiment of the invention, the foot locating member is fastened to the insole member along a periphery of the insole member, with the insole member being in contact with the ground and made from a deformable material.

In one embodiment of the invention, the one or more bracing members are pivotably coupled to the wearable shoe, through first apertures provided in upper portions of a left-side quarter portion and a right-side quarter portion of the wearable shoe, the first apertures aligning with second apertures provided in lower portions of the one or more bracing members.

In one embodiment of the invention, the offloading device further includes one or more liner pads provided on inner surfaces of the one or more bracing members, wherein the one or more liner pads are configured to make contact with skin of the user, wherein the one or more liner pads are made from a deformable material coated with a contact material, static coefficient of friction of the contact material ranging from 0.4 to 1.0, and kinetic coefficient of friction of the contact material ranging from 0.3 to 0.8.

In the context of the specification, the terms "polymer" or "plastic" refer to a material made up of long chains of organic molecules (having eight or more organic molecules) including, but not limited to, carbon, nitrogen, oxygen, and hydrogen as their constituent elements. The term polymer is envisaged to include both naturally occurring polymers such as wool, and synthetic polymers such as polyethylene and nylon.

In the context of the specification, the phrase "flexure hinges" refers to joints that are also known as "compliant mechanisms", "compliant hinges" or "elastic hinges", and are specialized components designed to permit controlled, limited rotation between two rigid bodies, about a specific axis while resisting movement in other directions. The controlled, limited rotation is achieved by using flexible elements (such as flexible sections with relatively smaller cross-sections than the bodies joined through the flexure hinges) instead of traditional rigid hinges. For example, flexure hinges may be generated by incorporating notches in a continuous piece of material to concentrate bending forces and create a well-defined pivot point.

BRIEF DESCRIPTION OF THE ACCOMPANYING DRAWINGS

The accompanying drawings illustrate the best mode for carrying out the invention as presently contemplated and set forth hereafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which.

DETAILED DESCRIPTION

Figure 1A:
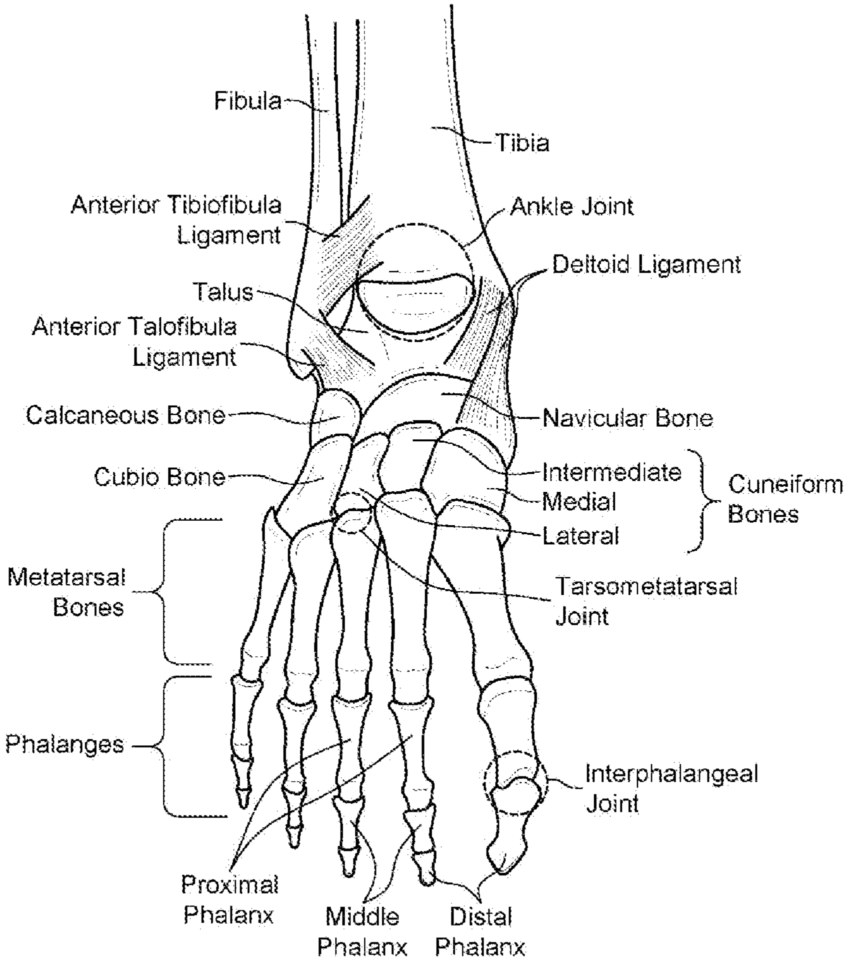
FIG. 1A illustrates the anatomy of bones surrounding an ankle joint of an average human being.

Embodiments of the present invention disclosure will be described more fully hereinafter with reference to the accompanying drawings in which like numerals represent like elements throughout the figures, and in which example embodiments are shown.

The detailed description and the accompanying drawings illustrate the specific exemplary embodiments by which the disclosure may be practiced. These embodiments are described in detail to enable those skilled in the art to practice the invention illustrated in the disclosure. It is to be understood that other embodiments may be utilized, and other changes may be made, without departing from the spirit or scope of the present disclosure. The following detailed description is therefore not to be taken in a limiting sense, and the scope of the present invention disclosure is defined by the appended claims. Embodiments of the claims may, however, be embodied in many different forms and should not be construed as limited to the embodiments set forth herein.

Embodiments of the present invention provide an offloading device for supporting an ankle joint of a user. The offloading device includes a locating member (also referred to as "the foot locating member") to locate therewithin the foot of the user. The locating member may be embodied as a rigid basal member with sidearms coupled thereto or may be embodied as a wearable shoe. Although not bindingly, an insole member may also be provided. The insole member may be fastened to the locating member to provide a cushion to the foot of the user. In several embodiments, the insole member may be a relatively thicker deformable member made from a deformable material such as foam. In several alternate embodiments, the insole member may be suspended through the lateral surfaces of the locating member, through stretchable or elastic fabric materials attached to the lateral surfaces of the locating member. The lateral surfaces may include left-side and right-side arm members in the embodiments including the rigid basal member, left-side and right-side quarter portions, a midsole member, or an outsole member in embodiments where the locating member has been embodied as a wearable shoe. The deformation of the insole member is envisaged to accommodate the bearing of the weight of the user by the offloading device, and also any extension in muscles and/or skin in the lower leg of the user during the acts of walking, running, jumping, etc.

Furthermore, one or more bracing members may be coupled to the locating member. The bracing members may be coupled to the locating member in such a manner that at least a relative rotation may be enabled between the bracing members and the locating member. In that regard, the one or more bracing members and the locating member may be coupled pivotably through holes/slots and pins, or hinge joints. In several alternate embodiments, the locating member and the one or bracing member may form a unitary structure and relative rotation may be enabled through flexure hinges. In several embodiments, through the provision of oblong slots, relative translation may also be possible between the bracing members and the locating member for height adjustment of the offloading device.

Inner surfaces of the bracing members may be provided with liner pads that would eventually be making contact with the lower leg of the user, in a region above the ankle joint. In that regard, the liner pads may be made from a deformable material, such as Neoprene, and may further be coated with a contact material with relatively high coefficients of friction, such as silicone materials. For example, the static coefficient of friction of the contact material may vary between 0.4 and 1.0 and the kinetic coefficient of friction of the contact material may vary between 0.3 and 0.8, with end values included in both cases.

Figure 1B:
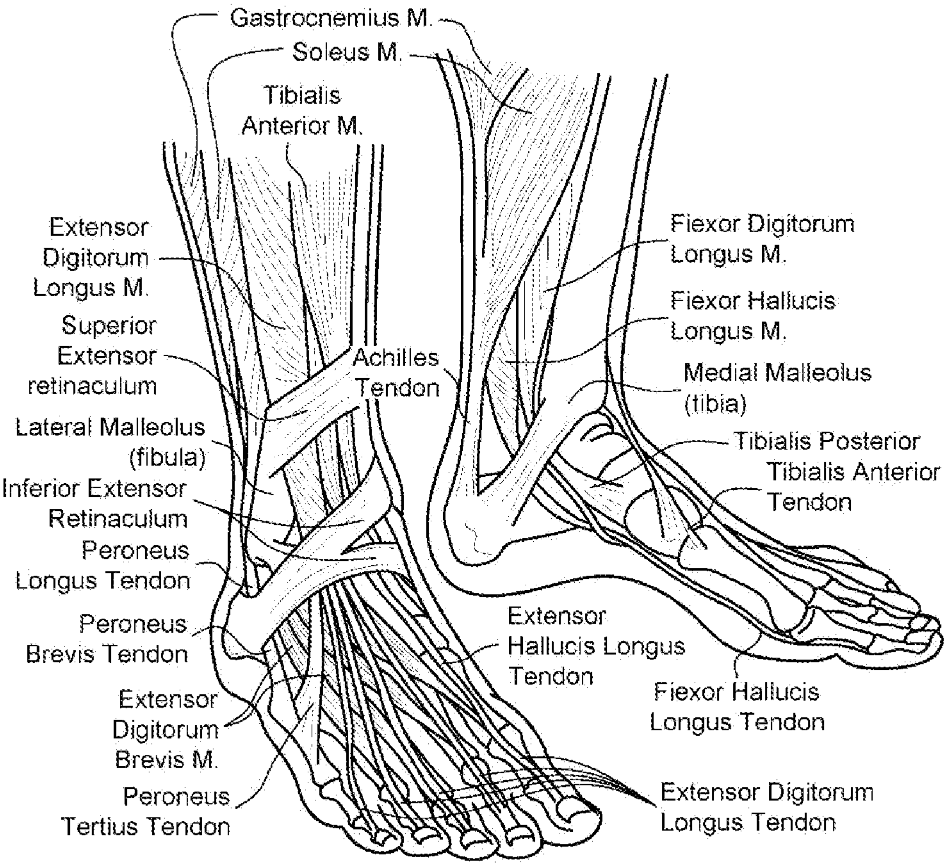
FIG. 1B illustrates the anatomy of muscles and tendons surrounding the ankle joint of the average human being.

The deformable material of the liner pads would provide sufficient cushion to the lower leg to not restrict the blood flow, whereas the high coefficients of friction of the contact material would provide enough grip for the calf muscles (See FIG. 1B) in the foot. Additionally, tightening between the bracing members and the lower leg may be provided by fastening arrangements that may include belts and/or straps with a loops and hooks fastening arrangement, a buckle and pin fastening arrangement, or a spring-loaded friction buckle fastening arrangement. In use, while walking, the reactionary forces applied by the ground to the locating member may be transferred to the region of the lower leg above the ankle joint through the bracing members and any stretching in the skin may be accommodated by the deformation of the bracing members and/or the insole member in the embodiments where the insole members would have been provided.

Several embodiments of the offloading device will now be discussed in detail with references to FIGS. 2A-9.

Figure 2A:
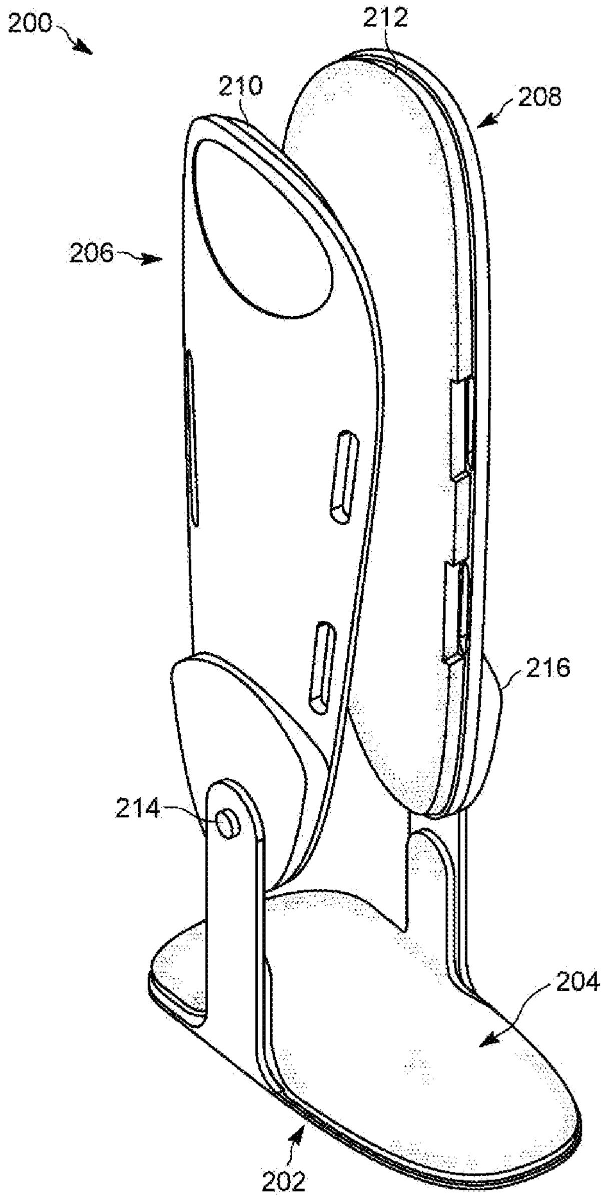
FIG. 2A illustrates a perspective view of an offloading device, in accordance with an embodiment of the present invention.
Figure 2B:
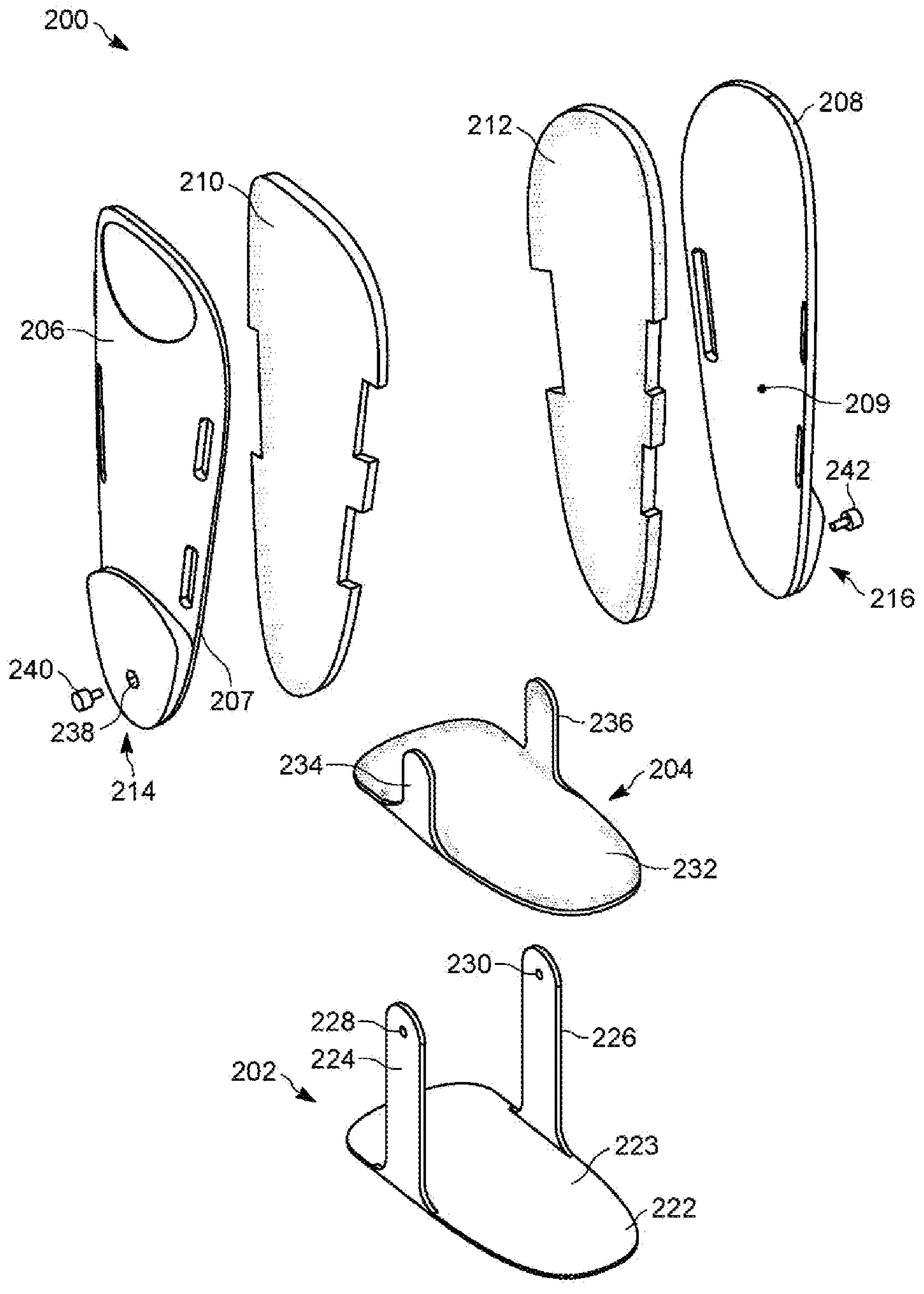
FIG. 2B illustrates an exploded view of the offloading device of FIG. 2A.

FIG. 2A illustrates a perspective view of an offloading device 200 (hereinafter also referred to as "the device 200"), in accordance with an embodiment of the present invention. FIG. 2B illustrates an exploded view of the offloading device 200 of FIG. 2A. The device 200 includes a foot locating member 202. The foot locating member 202 is configured to locate therewithin, the foot of the user. In other words, in use, the user would place or locate their foot within the foot locating member 202. Referring to FIG. 2B, the foot locating member 202 includes a basal locating member 222. Furthermore, a right-side arm member 224 and a left-side arm member 226 are coupled to the basal locating member 222 on the right and the left sides of the basal locating member 222, respectively. It is envisaged that at least the basal locating member 222 be made from a rigid material, such as thermoplastics (for example, polypropylene, nylon, thermoplastic polyurethane, etc.), thermosetting plastics (for example, phenolic resins, epoxy resins, etc.), composites (for example, carbon fiber, fiberglass), and metals (for example, steel, aluminum, etc.).

The right-side arm member 224 and the left-side arm member 226 may be molded as a unitary structure with the basal locating member 222 or may be made separately from the same or different materials and attached to the basal locating member 222 using material joining methods, such adhesive bonding, welding, soldering, brazing, etc. Furthermore, some flexure in right-side 224 and the left-side 226 arms members may be desirable to accommodate for plantar and dorsi flexion when the user is walking. A person skilled in the art would appreciate that the construction of the foot locating member 202 is not limited to the one shown in FIGS. 2A and 2B. On the contrary, the foot locating member 202 may assume several alternate constructions such as a wearable shoe (as will be illustrated later in the discussion), slippers, sandals, floaters, and the like, without departing from the scope of the invention.

The device 200 further includes an insole member 204 fastened to the foot locating member 202. In FIGS. 2A and 2B, the insole member 204 is provided above an upper surface 223 of the basal locating member 222. The insole member 204 includes a padding portion 232, a right-side suspension portion 234, and a left-side suspension portion 236. The padding portion 232 is configured to provide a cushion to the foot of the user. In that regard, the padding portion 232 may be made up of deformable materials such as foams (for example, polyurethane foam, memory foam, ethylene vinyl acetate foam, etc.), gels, cork, leather, wool, synthetic fabrics, or combinations thereof. The right-side suspension portion 234 and the left-side suspension portion

236 allow the insole member 204 or the padding portion 232 to be suspended from the right-side arm member 224 and the left-side arm member 226, respectively. In that regard, the right-side suspension portion 234 and the right-side suspension portion 236 may be made up of a stretchable fabric or an elastomer.

Furthermore, the device 200 includes one or more bracing members 206 and 208. The one or more bracing members 206 and 208 include a right-side bracing member 206 and a left-side bracing member 208. In several alternate embodiments of the invention, the right-side bracing member 206 and the left-side bracing member 208 may be combined as a unitary structure either covering the calf muscles of the lower leg of the user or covering the shin bone of the user. In several embodiments of the invention, the one or more bracing members 206 and 208 may be made from a rigid material selected from the group of possible materials for the basal locating member 222. The one or more bracing members 206 and 208 are configured to grasp, on the right side and the left side, a portion of the lower leg of the user, which is above the ankle joint.

Furthermore, the one or more bracing members 206 and 208 are pivotably coupled to the foot locating member 202. FIGS. 2A and 2B depict hinge joints 214 and 216 between the one or more bracing members 206 and 208, and the foot locating member 202, generated using second apertures 238 provided in lower portions of the one or more bracing members 206 and 208, first apertures 228 and 230 provided in upper portions of the right-side arm member 224 and the left-side arm member 226, respectively, and pins 240 and 242. The hinge joints 214 and 216 would allow the foot locating member 202 to rotate relative to the one or more bracing members 206 and 208 when the user would be walking, running, jumping, etc. The second apertures 238 have been depicted as circular holes. However, in several alternate embodiments, the second apertures 238 may be embodied as oblong or rectangular slots allowing for height adjustment of the device 200, allowing the device 200 to be customized for varying heights of several distinct users. Moreover, the hinge joints 214 and 216 may be replaced with other joints that allow relative rotation between two rigid bodies such as universal joints, flexure hinges (See FIGS. 5A and 5B), spherical joints, ball and socket joints, cylinder joints, bevel gear joints, etc. without departing from the scope of the invention.

One or more liner pads 210 and 212 may be provided on inner surfaces 207 and 209 of the one or more bracing members 206 and 208, respectively. The one or more liner pads 210 and 212 are configured to make contact with the skin of the user, in the portion of the lower leg that is located above the ankle joint of the user. In that regard, the one or more liner pads 210 and 212 may be made from a deformable material and coated with contact material with high static and kinetic coefficients of friction. The deformable material may be selected from a group consisting of neoprene, isoprene, silicones, polyurethane, spandex, etc. The contact material may further be skin friendly in addition to having high coefficients of friction, for example, silicone elastomers, hydrogels, and thermoplastic polyurethanes. It is further desirable, that the static coefficient of friction of the contact material ranges from 0.4 to 1.0, and the kinetic coefficient of friction of the contact material ranges from 0.3 to 0.8 for better grip and offloading of reactionary ground forces to the lower portion of the leg located above the ankle joint.

Figure 3A:
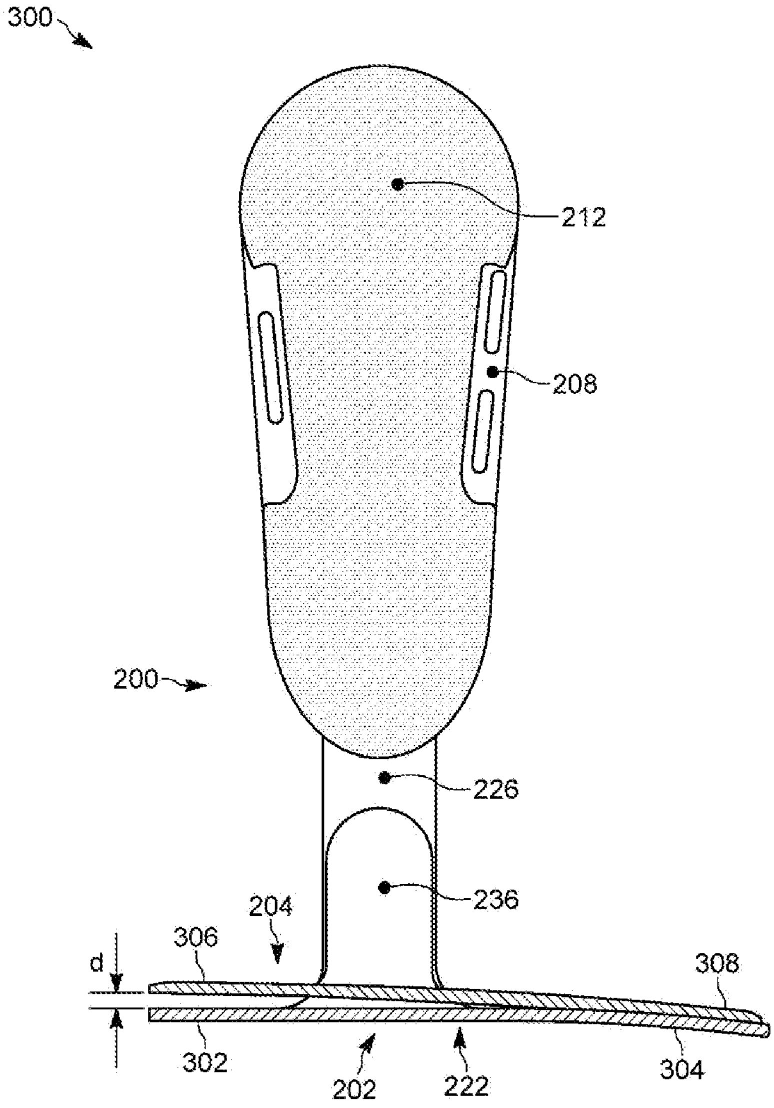
FIG. 3A illustrates a left-side sectional view of the offloading device, in accordance with an embodiment of the present invention.

FIG. 3A illustrates a left-side sectional view 300 of the offloading device 200, in accordance with an embodiment of the present invention. The basal locating member 222 includes a posterior locating portion 302 and an anterior locating portion 304. Similarly, the insole member 204 includes an insole posterior portion 306 and an insole anterior portion 308. It is envisaged that during weight bearing and/or dorsi flexion when combined with weight bearing (such as during walking, running, and/or jumping), at least the insole posterior portion 306 undergoes deformation within a predetermined range. In that regard, a predefined clearance d (for example, between 5 mm and 25 mm) may be provided between the posterior locating portion 302 and the insole posterior portion 306.

Figure 3B:
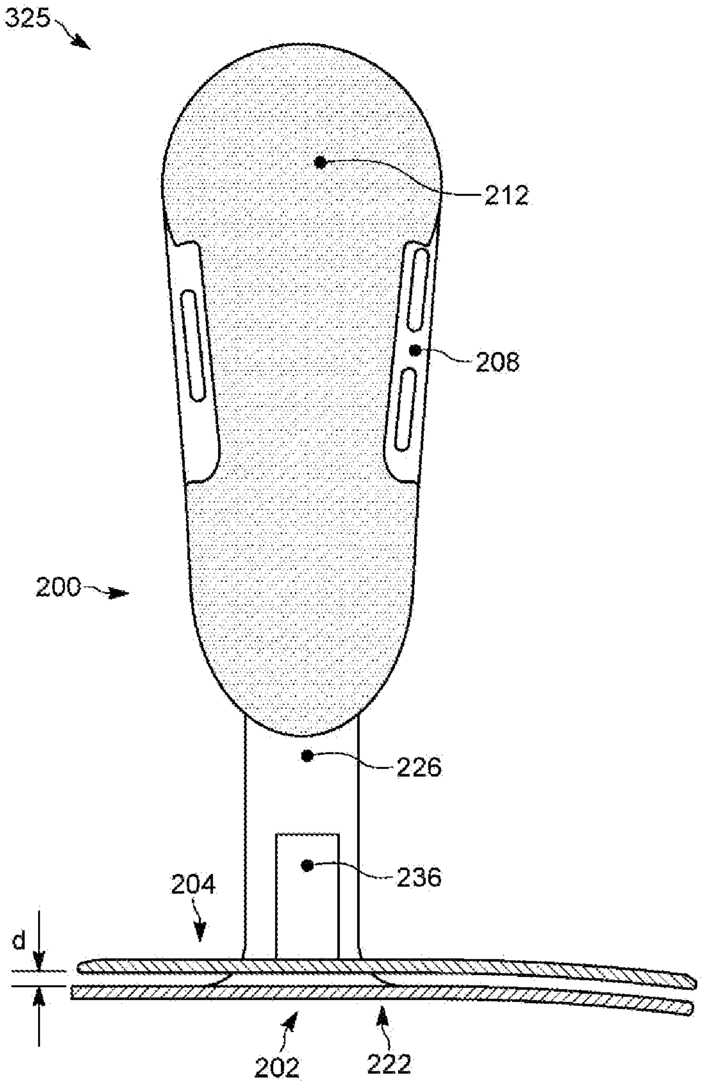
FIG. 3B illustrates a left-side sectional view of the offloading device, in accordance with another embodiment of the present invention.

FIG. 3B illustrates a left-side sectional view 325 (or "the view 325") of the offloading device 200, in accordance with another embodiment of the present invention. In the view 325, the predefined clearance d between the insole member 204 and the basal locating member 202 has been provided along the entire lengths of the insole member 204 and the basal locating member 222. The predefined clearance d allows to accommodate for stretching in the skin while walking, in the portion of the lower leg above the ankle joint, when the one or more bracing members 206 and 208 have held the lower leg firmly.

Figure 3C:
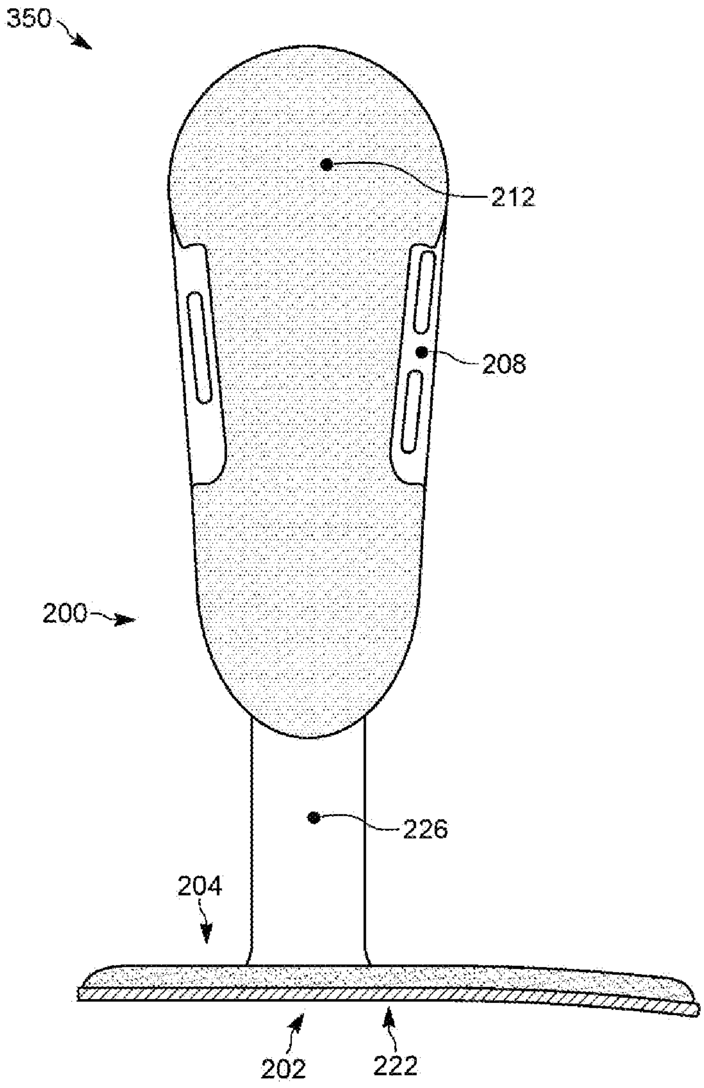
FIG. 3C illustrates a left-side sectional view of the offloading device, in accordance with yet another embodiment of the present invention.

FIG. 3C illustrates a left-side sectional view 350 (or "the view 350") of the offloading device 200, in accordance with yet another embodiment of the present invention. In the offloading device 200 of the view 350, there is no clearance provided between the insole member 204 and the basal locating member 222, and the insole member 204 is in contact with and bonded to the basal locating member 222 along the entire lengths of the insole member 204 and the basal locating member 222. Instead, the insole member 204 has been provided with relatively greater thickness to accommodate for the stretching of the skin of the lower leg.

Figure 4A:
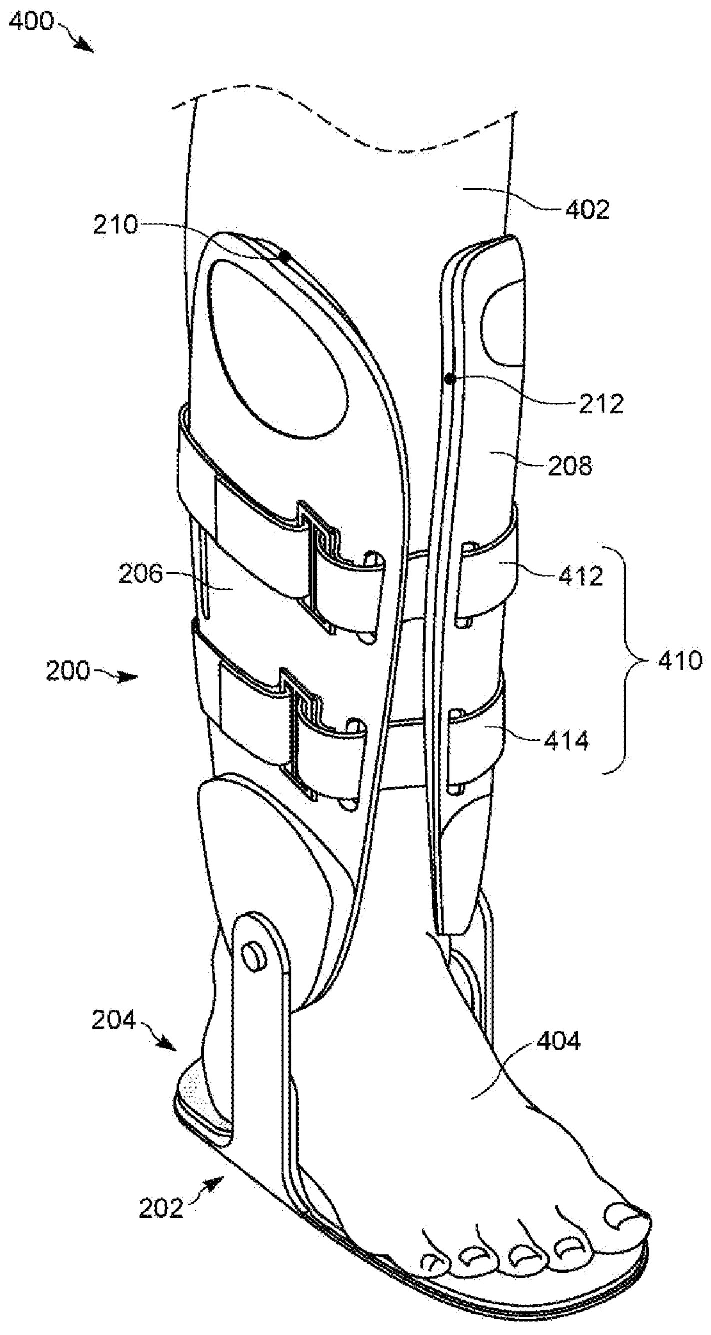
FIG. 4A illustrates a first application scenario of the offloading device, in accordance with an embodiment of the present invention.

FIG. 4A illustrates a first application scenario 400 of the offloading device 200, in accordance with an embodiment of the present invention. The foot 404 of the user has been located within the foot locating member 202 and upon the insole member 204. Furthermore, the one or more bracing members 206 and 208 have been fastened to a portion 402 of the lower leg that is above the ankle joint, using a fastening arrangement 410. In several embodiments of the invention, the fastening arrangement 410 includes a plurality of belts and/or a plurality of straps 412 and 414. The plurality of belts and/or the plurality of straps 412 and 414 may further be provided with one or more of a loops and hooks fastening arrangement (also known as "Velcro®"), a buckle pin and holes fastening arrangement, and a spring-loaded friction buckle fastening arrangement.

Figure 1C:
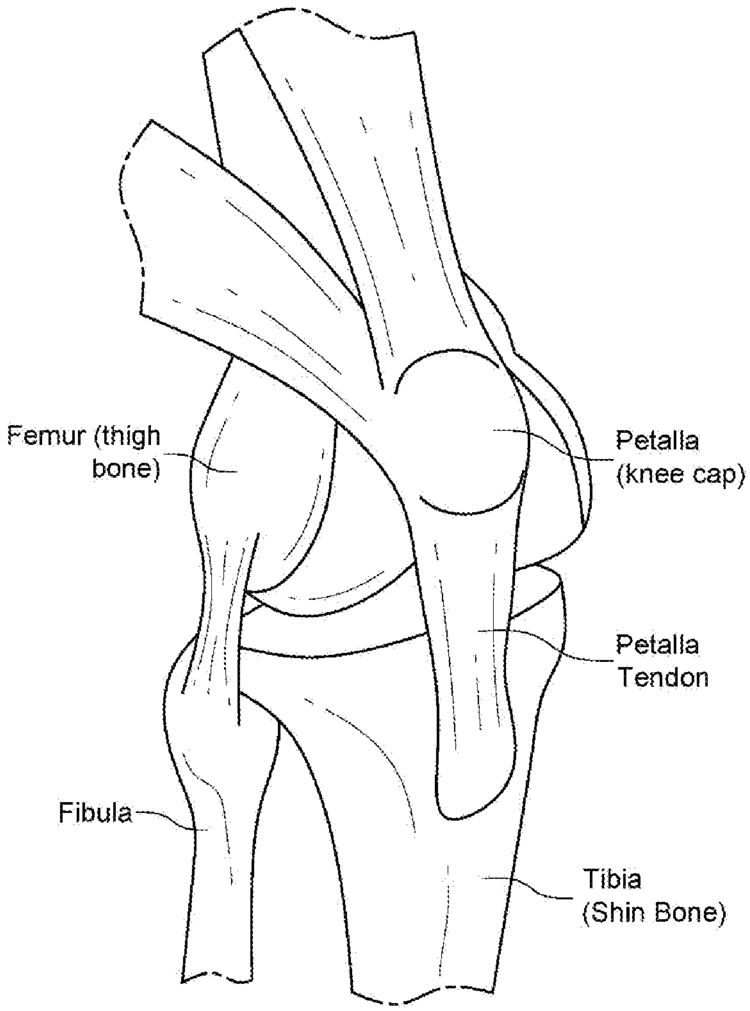
FIG. 1C illustrates the anatomy of a knee joint of the average human being.
Figure 4B:
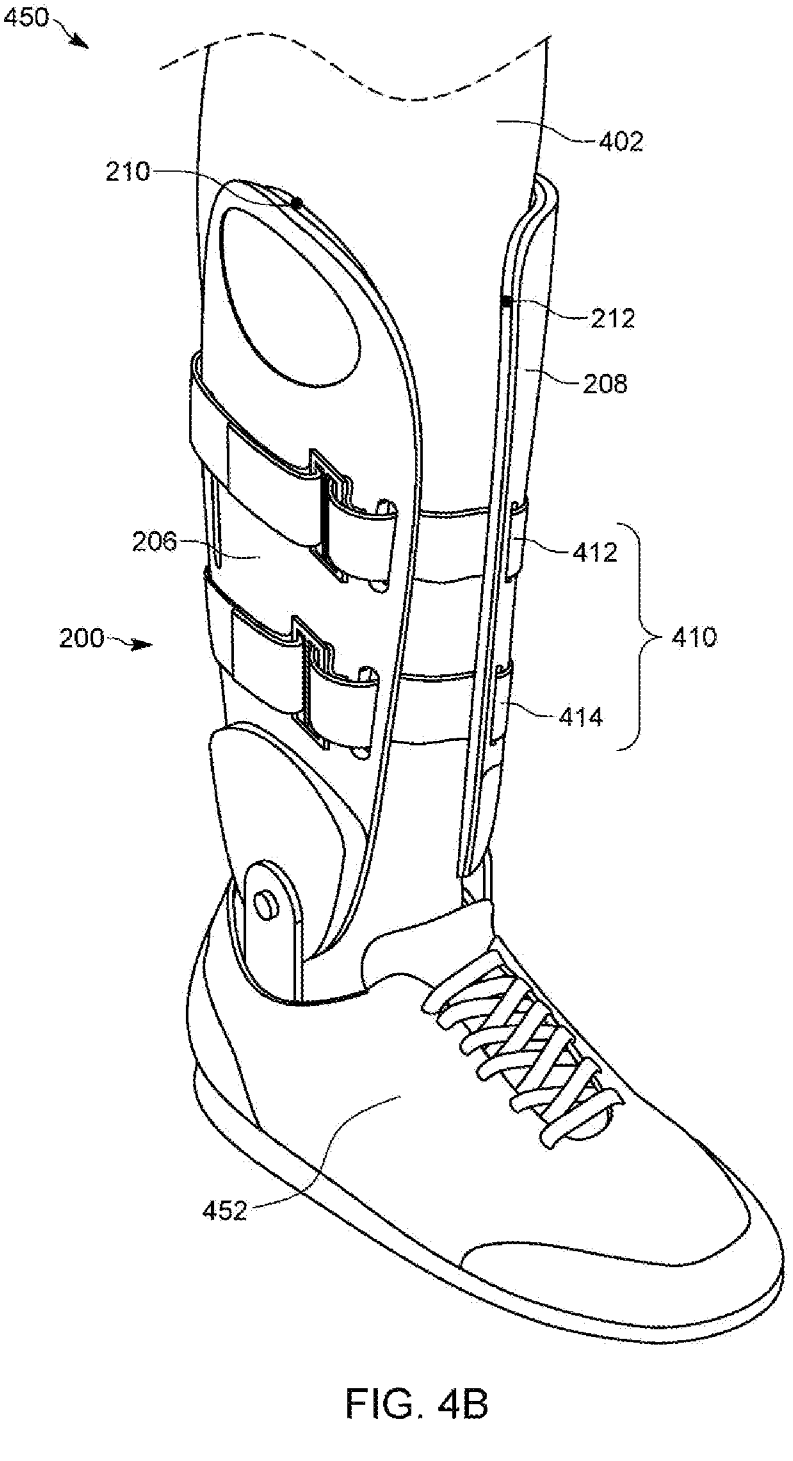
FIG. 4B illustrates a second application scenario of the offloading device, in accordance with an embodiment of the present invention.

On tightening the fastening arrangement 410, the one or more liner pads 210 and 212 grasp the skin of the portion 402. When a user walks, runs, jumps, etc. the reactionary force applied by the ground is transferred through the foot locating member 202, the one or more bracing members 206 and 208, and the one or more liner pads 210 and 212, to a great extent to gastrocnemius (calf), soleus, and anterior tibialis muscles (See FIG. 1B). In some embodiments with extended lengths of the one or more bracing members 206 and 208, the reactionary force may be transferred, possibly, to some extent to the patellar tendon (See FIG. 1C). Therefore, only a partial or no amount of force is applied to the ankle joint (See FIGS. 1A and 1B). FIG. 4B illustrates a second application scenario 450 of the offloading device 200, in accordance with an embodiment of the present invention. FIG. 4B illustrates that the construction of the device 200 depicted through FIGS. 2A-3C has an added advantage that a wearable shoe 452 can be worn over the foot locating member 202 and the insole member 204.

Figure 5A:
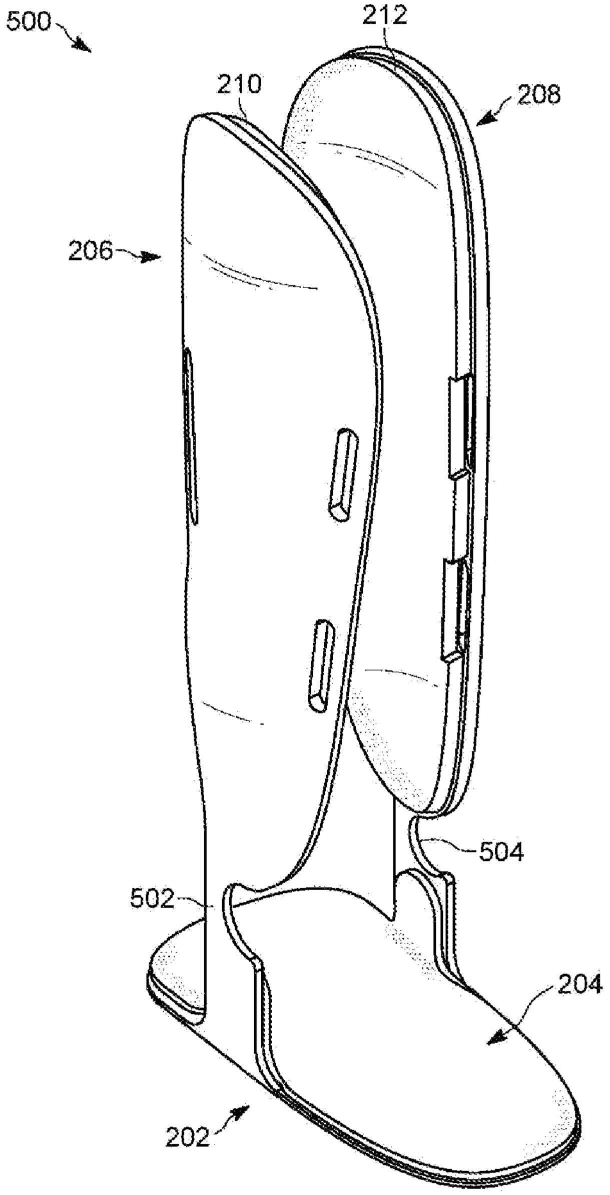
FIG. 5A illustrates a perspective view of the offloading device, in accordance with another embodiment of the present invention.
Figure 5B:
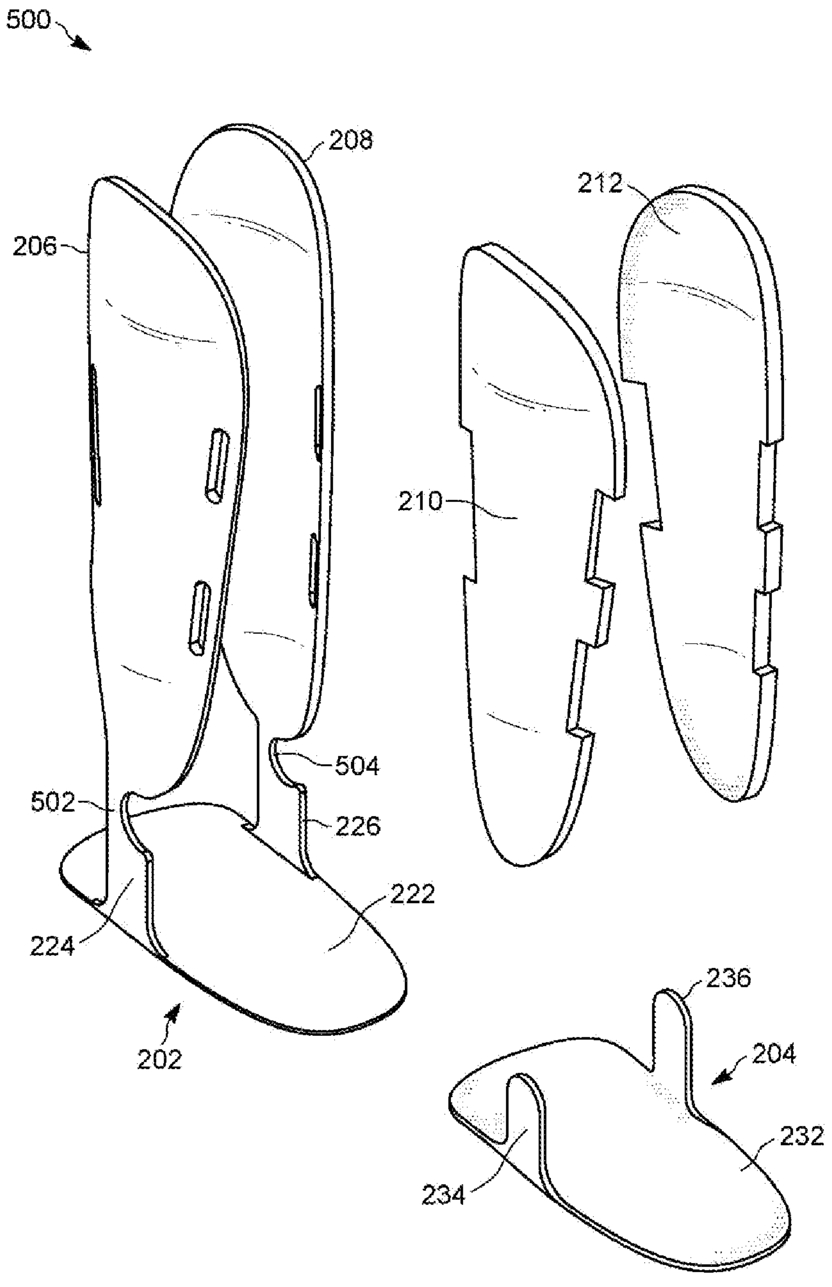
FIG. 5B illustrates an exploded view of the offloading device of FIG. 5A.

FIG. 5A illustrates a perspective view of an offloading device 500 (hereinafter also referred to as "the device 500"), in accordance with another embodiment of the present invention. FIG. 5B illustrates an exploded view of the offloading device 500 of FIG. 5A. Referring to FIGS. 5A and 5B, the offloading device 500 depicts the one or more bracing members 206 and 208 and the foot supporting member 202 in the form of a unitary structure. Furthermore, flexure hinges 502 and 504 provided at the right side and the left side, respectively, of the foot locating member 202 allow pivotable coupling between the one or more bracing members 206 and 208, and the foot locating member 202. Other members of the device 500 such as the one or more liner pads 210 and 212, the insole member 204, the fastening arrangement 410 may function identically as described for the offloading device 200.

Figure 6A:
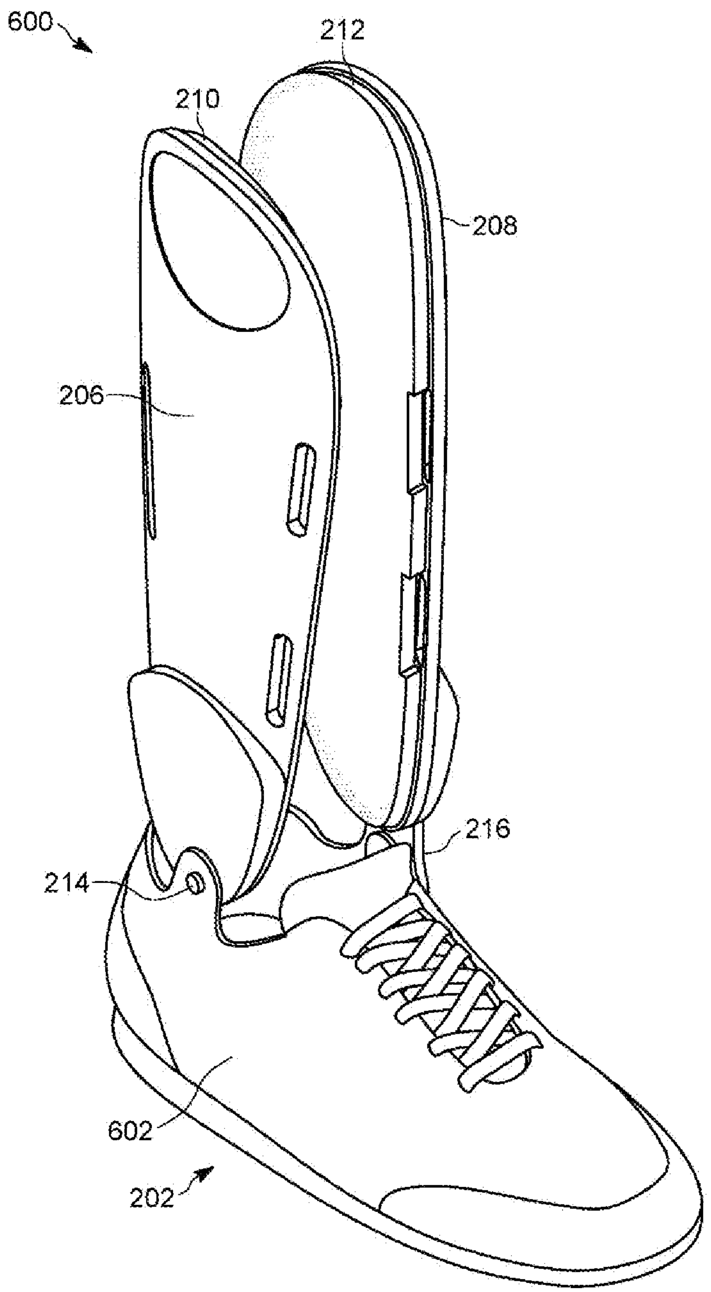
FIG. 6A illustrates a perspective view of the offloading device, in accordance with yet another embodiment of the present invention.
Figure 6B:
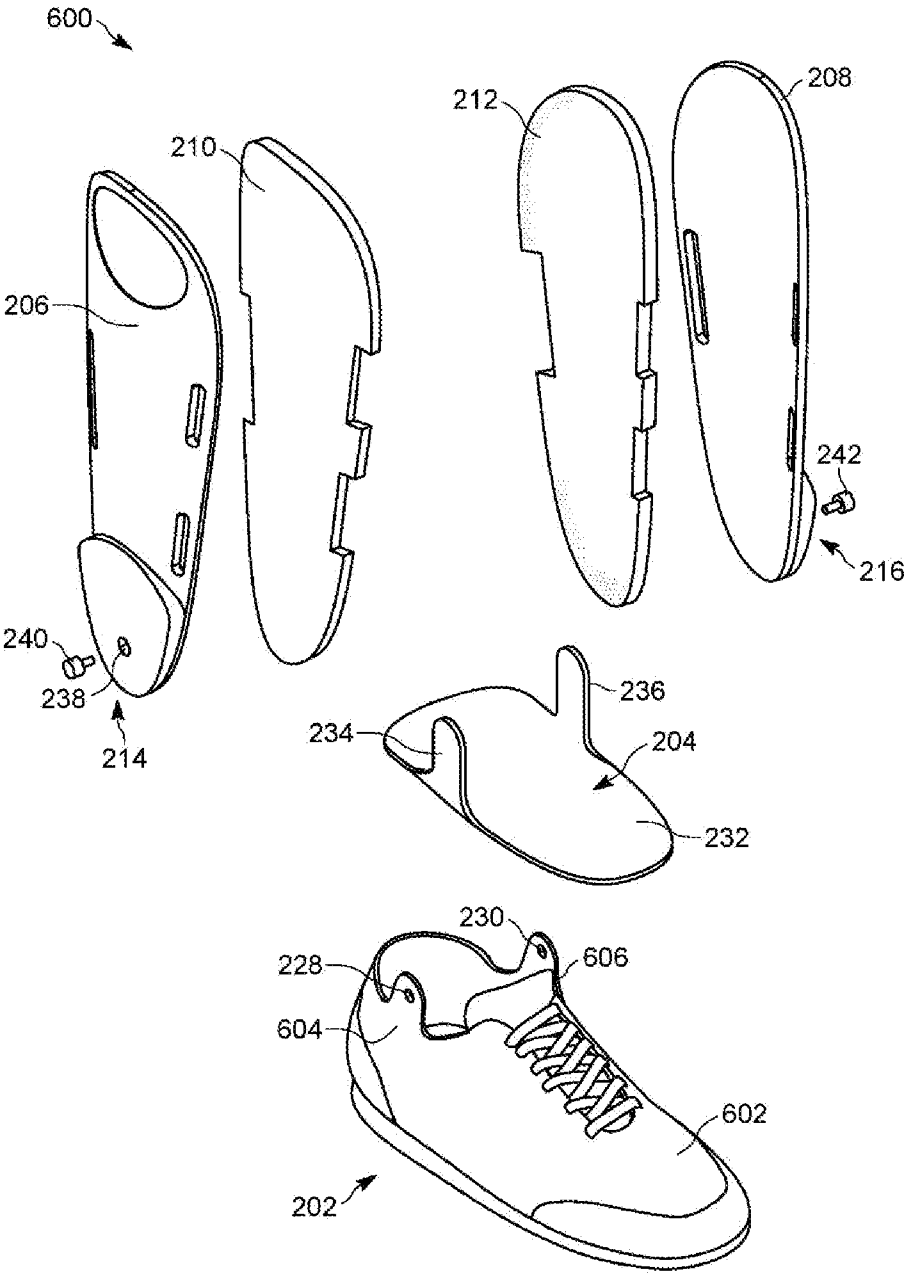
FIG. 6B illustrates an exploded view of the offloading device of FIG. 6A.

FIG. 6A illustrates a perspective view of an offloading device 600 (hereinafter also referred to as "the device 600"), in accordance with yet another embodiment of the present invention. FIG. 6B illustrates an exploded view of the offloading device 600 of FIG. 6A. Referring to FIGS. 6A and 6B, the device 600 differs from the device 200 in the manner that the foot locating member 202 is embodied as a wearable shoe 602. Other components such as the hinge joints 214 and 216, the one or bracing members 206 and 208, the one or more liner pads 210 and 212, and the fastening arrangement 410 may take forms that are identical to the device 200. Furthermore, the first apertures 228 and 230 are provided in upper portions of the right-side quarter portion 604 and the left-side quarter portion 606 of the wearable shoe 602. The first apertures 228 and 230 align with the second apertures 238 provided in the lower portions of the one or more bracing members 206 and 208.

Figure 7A:
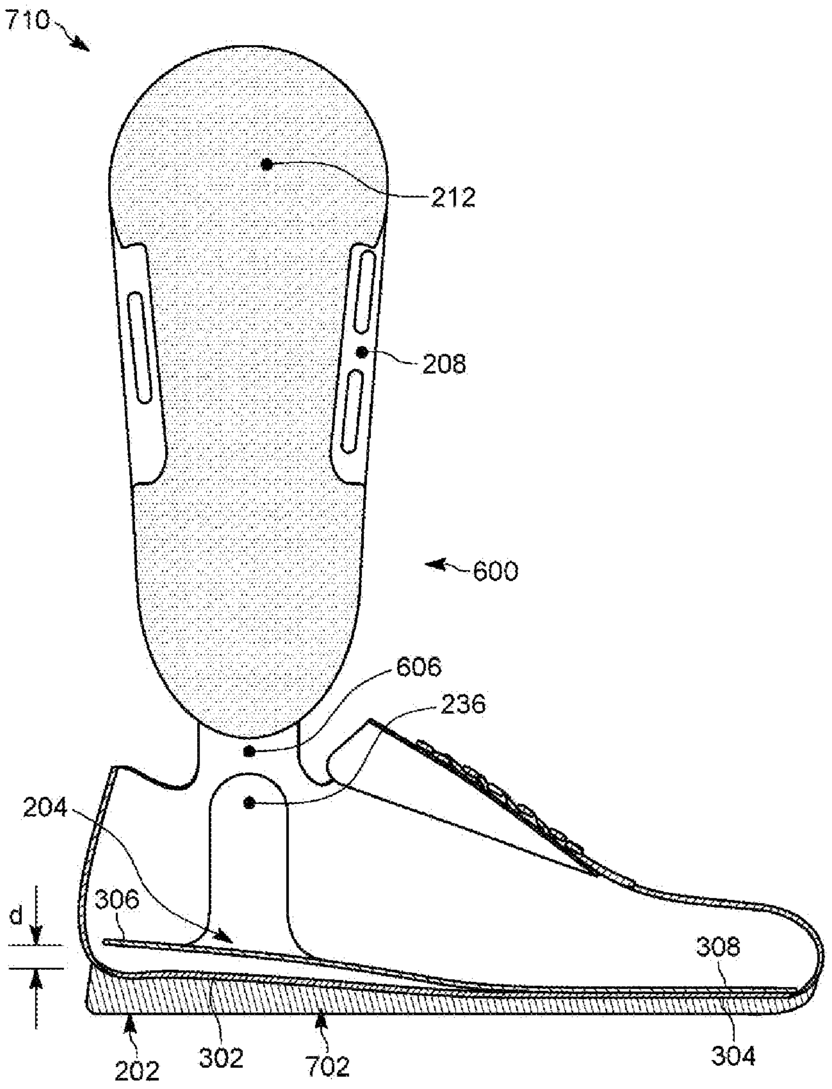
FIG. 7A illustrates a left-side sectional view of the offloading device, in accordance with an embodiment of the present invention.

FIG. 7A illustrates a left-side sectional view 710 of the offloading device 600, in accordance with an embodiment of the present invention. The basal locating member 222 has an equivalent in the form of a midsole member 702 of the wearable shoe 602. Therefore, the midsole member 702 is envisaged to include the posterior locating portion 302 and the anterior locating portion 304. Similarly, the insole member 204 includes the insole posterior portion 306 and the insole anterior portion 308. In that regard, the predefined clearance d has been provided between the posterior locating portion 302 and the insole posterior portion 306. Furthermore, the left-side suspension portion 236 is attached to the left-side quarter portion 606. Similarly, although not shown in FIG. 7A, the right-side suspension portion 234 would be attached to the right-side quarter portion 604.

Figure 7B:
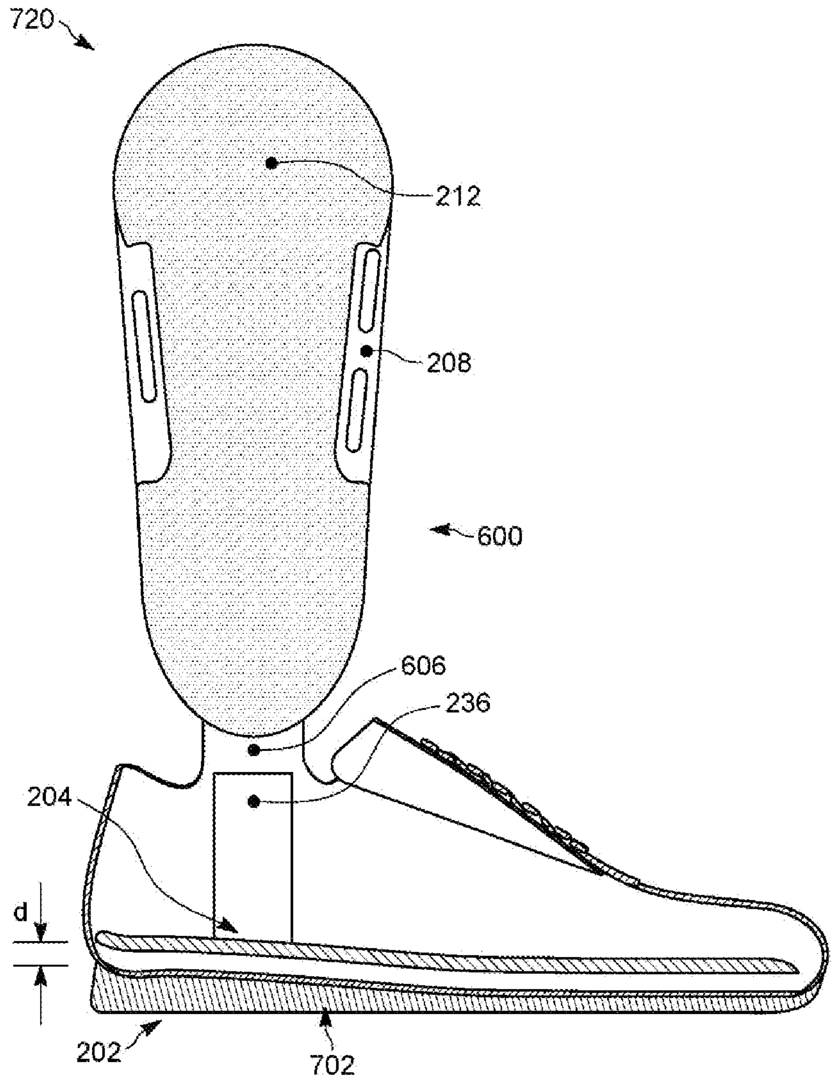
FIG. 7B illustrates a left-side sectional view of the offloading device, in accordance with another embodiment of the present invention.

FIG. 7B illustrates a left-side sectional view 720 (or "the view 720") of the offloading device 600, in accordance with another embodiment of the present invention. In the view 720, the predefined clearance d between the insole member 204 and the midsole member 702 has been provided along the entire lengths of the insole member 204 and the midsole member 702. The predefined clearance d allows to accommodate for stretching in the skin while walking, in the portion of the lower leg above the ankle joint, when the one or more bracing members 206 and 208 have held the lower leg firmly. Through FIGS. 7A and 7B, it can be observed that at least the insole posterior portion 306 is suspended from lateral surfaces, i.e. the left-side quarter portion 606 and the right-side quarter portion 604, of the foot locating member 202 embodied as the wearable shoe 602. In addition, at least the insole posterior portion 306 has the predefined clearance d above the midsole portion 702.

Figure 7C:
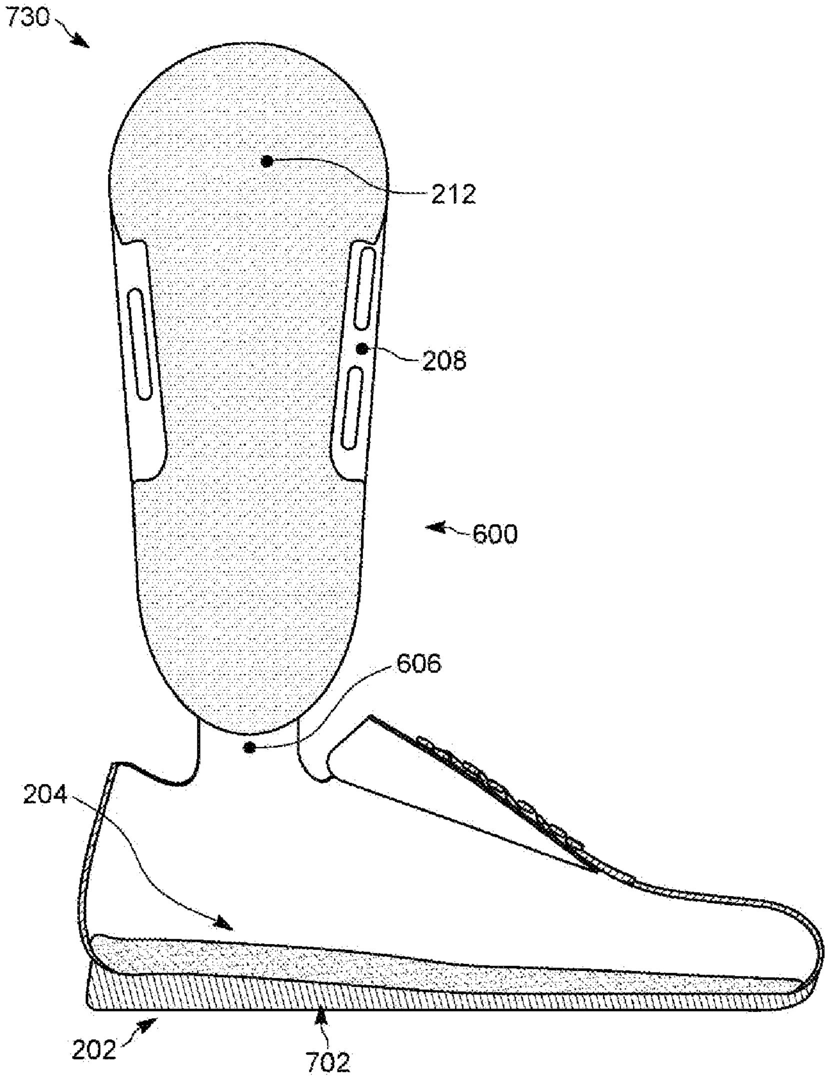
FIG. 7C illustrates a left-side sectional view of the offloading device, in accordance with another embodiment of the present invention.

FIG. 7C illustrates a left-side sectional view 730 (or "the view 730") of the offloading device 600, in accordance with another embodiment of the present invention. In the offloading device 600 of the view 730, there is no clearance provided between the insole member 204 and the midsole member 702. Furthermore, the insole member 204 is in contact with and bonded to the midsole member 702 along the entire lengths of the insole member 204 and the foot locating member 202 (or the midsole member 702). Instead, the insole member 204 has been provided with relatively greater thickness to accommodate for the stretching of the skin of the lower leg.

Figure 7D:
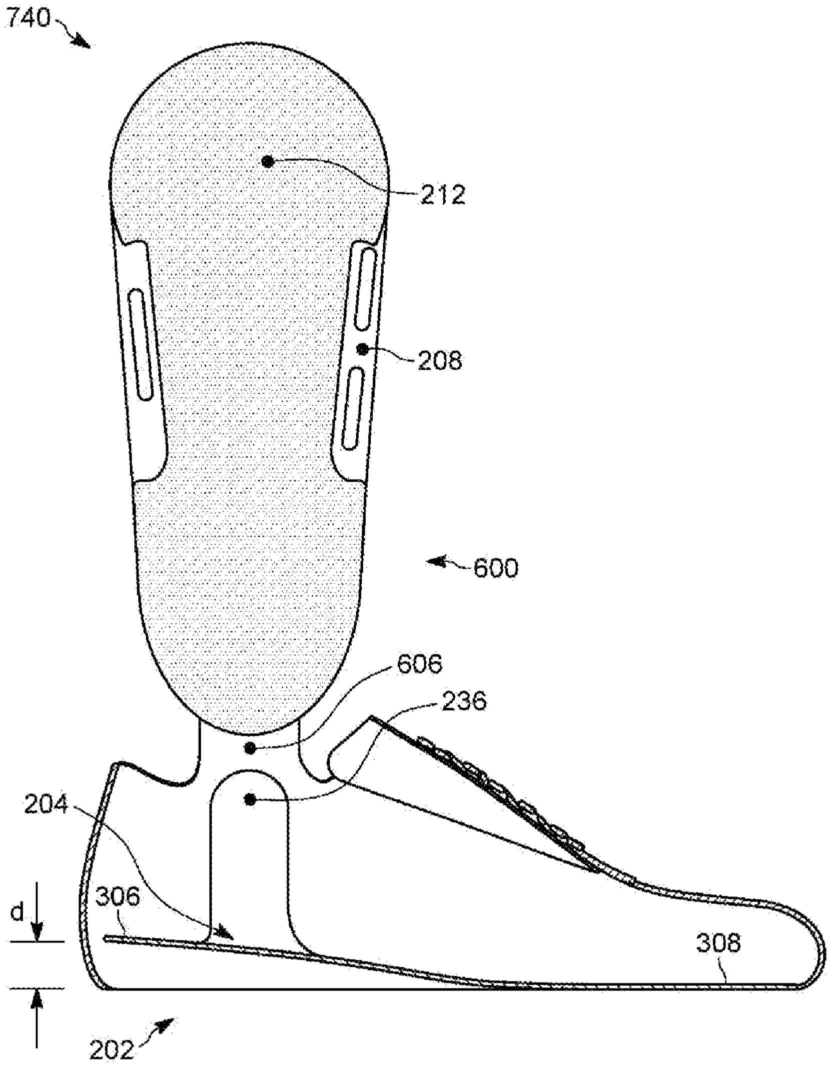
FIG. 7D illustrates a left-side sectional view of the offloading device, in accordance with another embodiment of the present invention.

FIG. 7D illustrates a left-side sectional view 740 (or "the view 740") of the offloading device 600, in accordance with another embodiment of the present invention. The predefined clearance d has been provided between ground and the insole posterior portion 306. Furthermore, the left-side suspension portion 236 is attached to the left-side quarter portion 606. Similarly, the right-side suspension portion 234 would be attached to the right-side quarter portion 604. Therefore, the foot locating member 202 may be connected along a periphery of the padding portion 232 of the insole member 202. Alternately, the midsole member 702 or an outsole member (not shown), of the foot locating member 202 embodied as the wearable shoe 602, may be connected to the insole member 204 along the periphery of the insole member 204 (See FIG. 7F). In that regard, the padding portion 232 may be directly woven or bonded to the midsole member 702 or the outsole member (not shown).

Figure 7E:
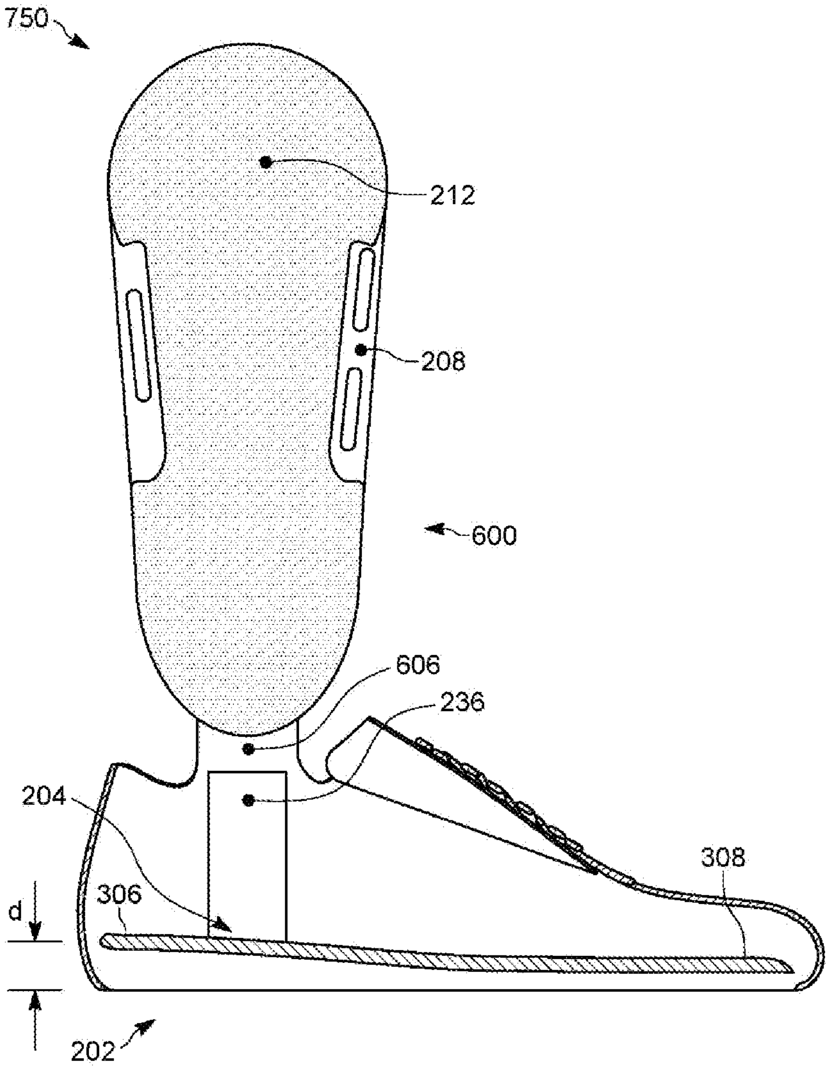
FIG. 7E illustrates a left-side sectional view of the offloading device, in accordance with another embodiment of the present invention.

FIG. 7E illustrates a left-side sectional view 750 (or "the view 750") of the offloading device 600, in accordance with another embodiment of the present invention. In the view 750, the predefined clearance d between the insole member 204 and ground has been provided along the entire length of the insole member 204. The predefined clearance d allows to accommodate for stretching in the skin while walking, in the portion of the lower leg above the ankle joint, when the one or more bracing members 206 and 208 have held the lower leg firmly. Furthermore, in several alternate embodiments, the foot locating member 202 embodied as the wearable shoe 602, may be connected to the insole member 204 along the periphery of the insole member 204. The connection between the insole member 204 and the foot locating member 202 may be achieved through the right-side suspension portion 234 and the left-side suspension portion 236 using weaving or adhesive bonding with the right-side quarter portion 604 and the left-side quarter portion 606, respectively. Alternately, the padding portion 232 may be directly woven or bonded to the midsole member 702 or the outsole member (not shown).

Figure 7F:
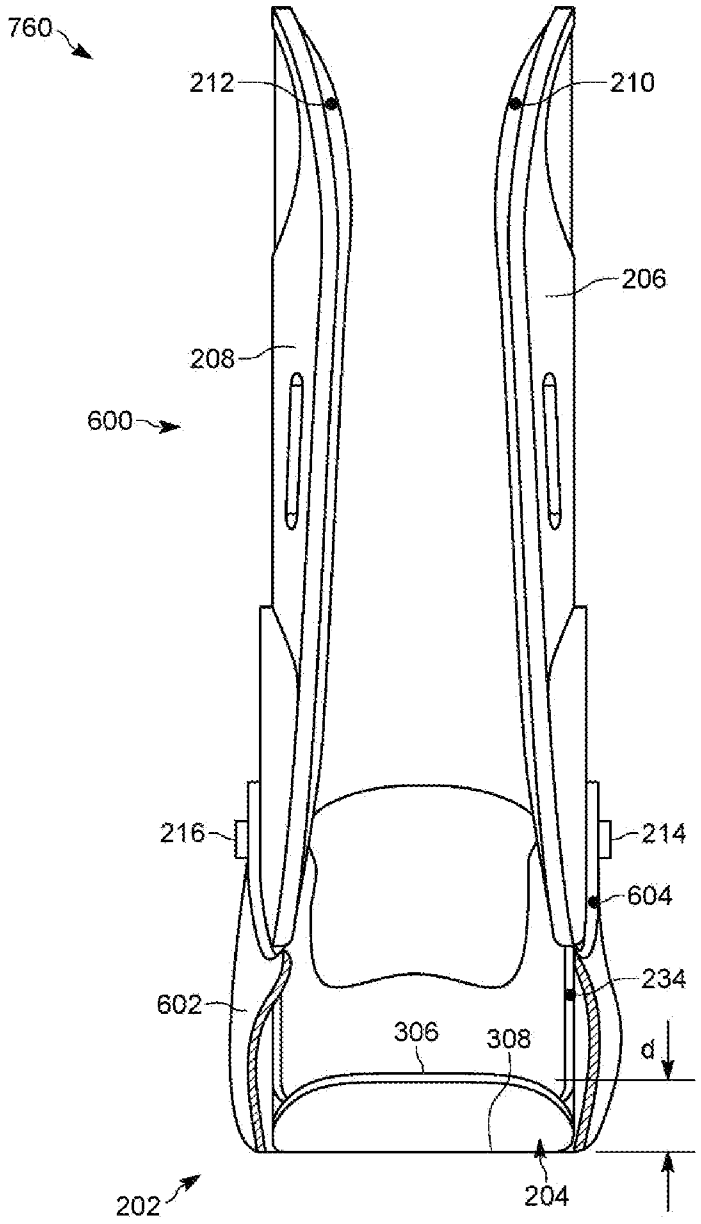
FIG. 7F illustrates a mid-sectional view of the offloading device, in accordance with another embodiment of the present invention.

FIG. 7F illustrates a mid-sectional view 760 (or "the view 760") of the offloading device 600, in accordance with another embodiment of the present invention. The view 760 illustrates that the foot locating member 202 is connected along the periphery of the insole member 204. In several embodiments of the invention, the midsole member 702 or an outsole member (not shown), of the foot locating member 202 embodied as the wearable shoe 602, may be connected along the periphery of the insole member 204. The connection between the insole member 204 and the foot locating member 202 may be achieved through the right-side suspension portion 234 and the left-side suspension portion 236 using weaving or adhesive bonding with the right-side quarter portion 604 and the left-side quarter portion 606, respectively. Alternately, the padding portion 232 may be directly woven or bonded to the midsole member 702 or the outsole member (not shown). Moreover, at least the insole posterior portion 306 has the predefined clearance d above the ground and is configured to undergo deformation within the predetermined range because of the predefined clearance d.

Figure 7G:
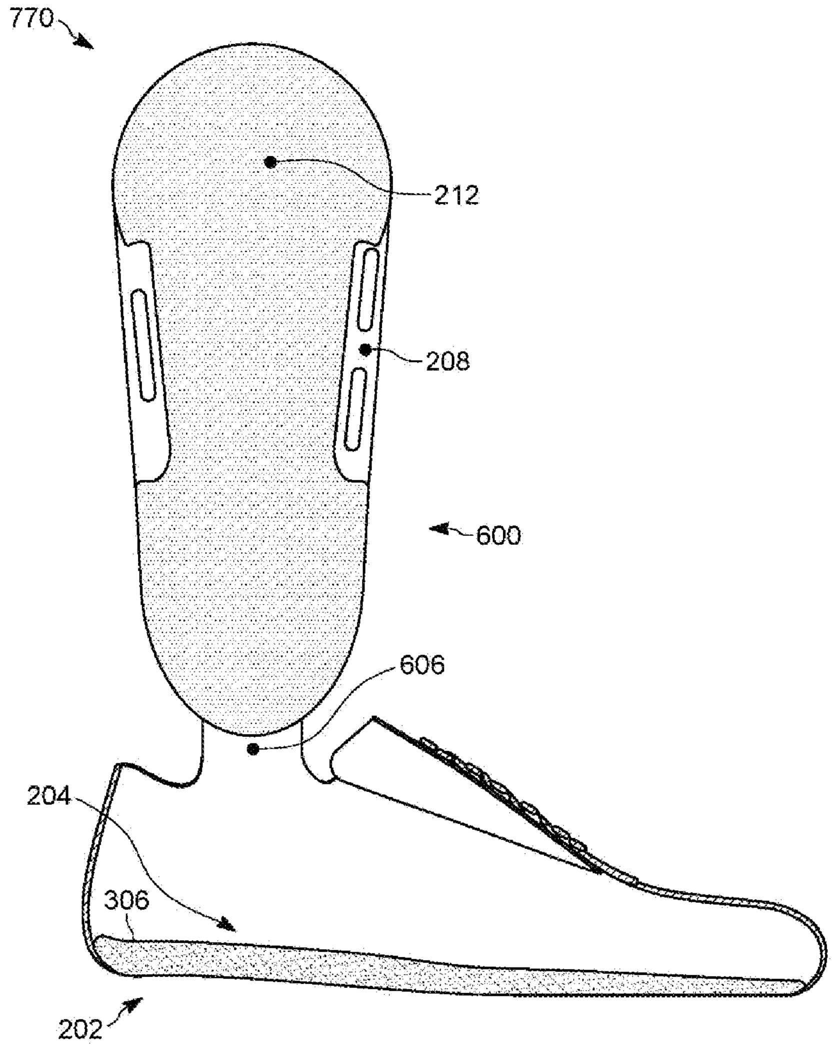
FIG. 7G illustrates a left-side sectional view of the offloading device, in accordance with another embodiment of the present invention.

FIG. 7G illustrates a left-side sectional view 770 (or "the view 770") of the offloading device 600, in accordance with another embodiment of the present invention. In the offloading device 600 of the view 770, there is no clearance provided between the insole member 204 and the ground. On the contrary, the insole member 204 is in contact with the ground along the entire length of the insole member 204. Instead, the insole member 204 has been provided with greater thickness to accommodate for the stretching of the skin of the lower leg.

Figure 7H:
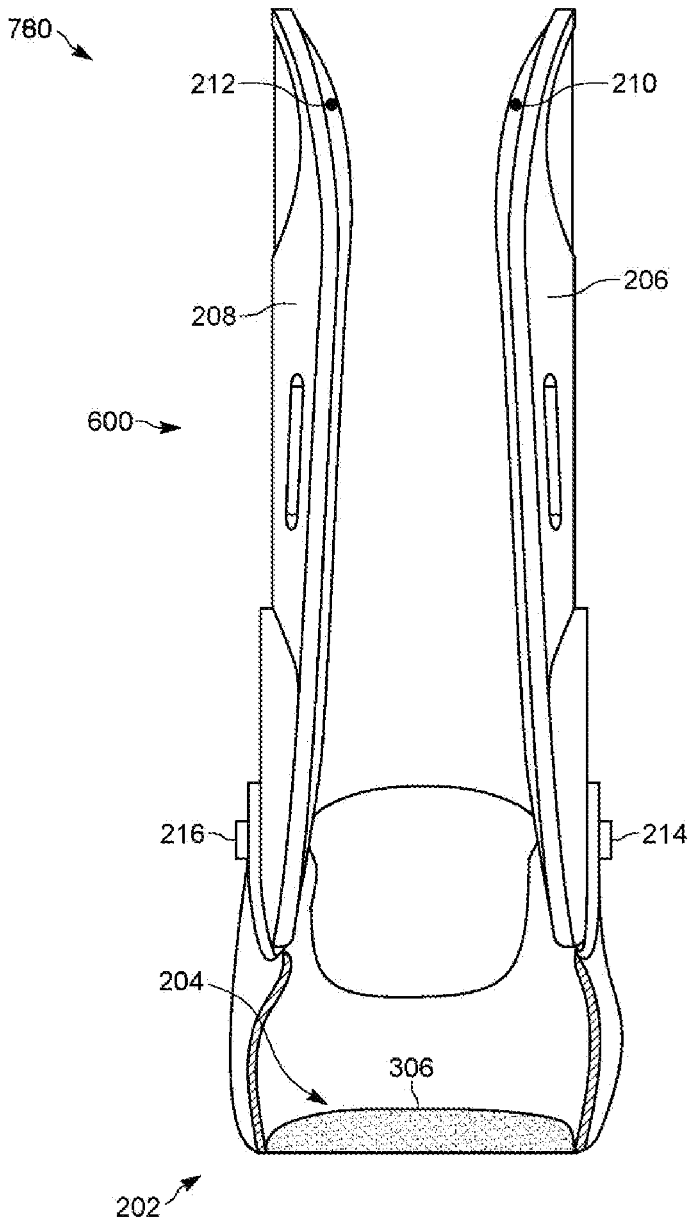
FIG. 7H illustrates a mid-sectional view of the offloading device, in accordance with another embodiment of the present invention.

FIG. 7H illustrates a mid-sectional view 780 (or "the view 780") of the offloading device 600, in accordance with another embodiment of the present invention. The view 780 illustrates that the foot supporting member 202 is connected along the periphery of the insole member 204. In several embodiments, the midsole member 702 or an outsole member (not shown), of the foot locating member 202 embodied as the wearable shoe 602, may be connected along the periphery of the insole member 204. The connection between the insole member 204 and the foot locating member 202 may be achieved through the right-side suspension portion 234 and the left-side suspension portion 236 using weaving or adhesive bonding with the right-side quarter portion 604 and the left-side quarter portion 606, respectively. Alternately, the padding portion 232 may be directly woven or bonded to the midsole member 702 or the outsole member (not shown). Moreover, the insole member 204 is configured to undergo deformation within the predetermined range because of the relatively greater thickness of the insole member 204.

Figure 7I:
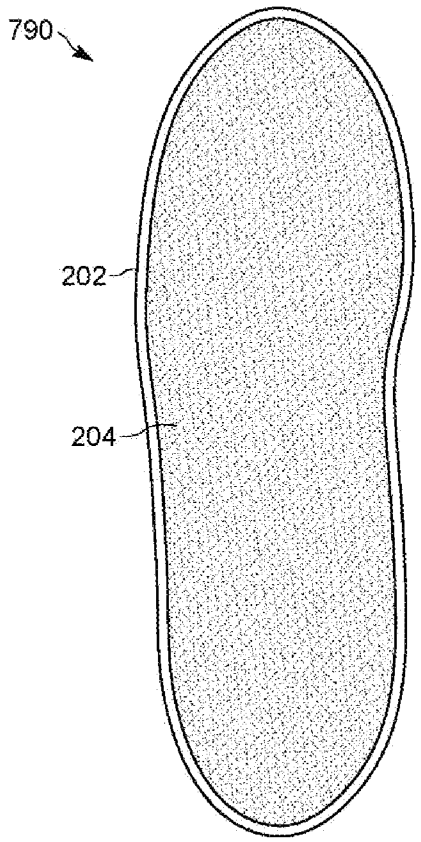
FIG. 7I illustrates a bottom view of the offloading device, in accordance with another embodiment of the present invention.

FIG. 7I illustrates a bottom view 790 (or "the view 790") of the offloading device 600, in accordance with another embodiment of the present invention. The view 790 illustrates the insole member 204. The view 790 illustrates that the foot locating member 202 is connected along the periphery of the insole member 204. In several embodiments of the invention, the midsole member 702 or an outsole member (not shown), of the foot locating member 202 embodied as the wearable shoe 602, may be connected along the periphery of the insole member 204. The connection between the insole member 204 and the foot locating member 202 may be achieved through the right-side suspension portion 234 and the left-side suspension portion 236 using weaving or adhesive bonding with the right-side quarter portion 604 and the left-side quarter portion 606, respectively. Alternately, the padding portion 232 may be directly woven or bonded to the midsole member 702 or the outsole member (not shown). Embodiments disclosed in FIGS. 7D to 7I have an added advantage that they allow the predefined clearance d and/or additional relative thickness of the insole member 204 to be incorporated into the offloading device 600, without modifying an overall height of the wearable shoe 602.

Figure 8:
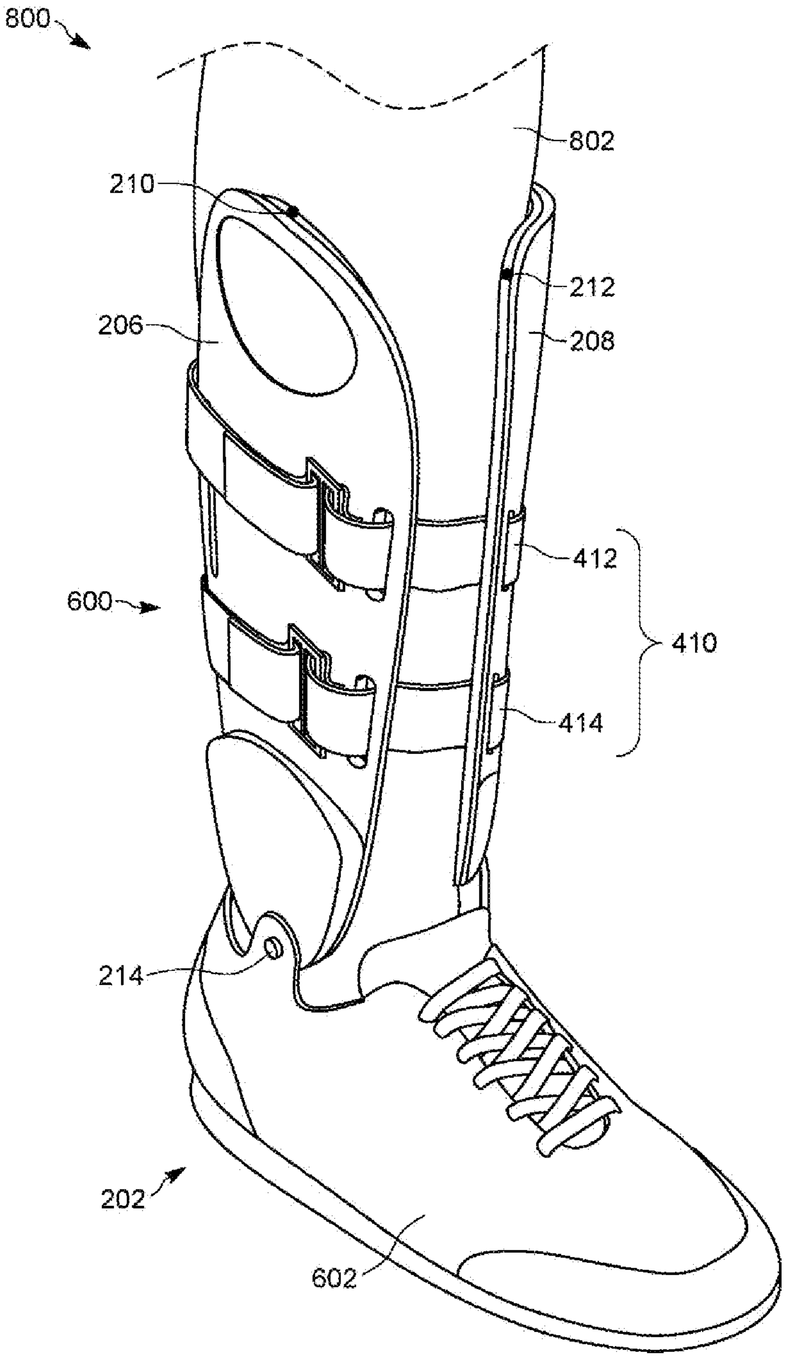
FIG. 8 illustrates an application scenario of the offloading device, in accordance with another embodiment of the present invention.

FIG. 8 illustrates an application scenario 800 of the offloading device 600, in accordance with another embodiment of the present invention. The foot of the user has been located within the wearable shoe 602. Furthermore, the one or more bracing members 206 and 208 have been fastened to a portion 802 of the lower leg that is above the ankle joint, using the fastening arrangement 410. In several embodiments of the invention, the fastening arrangement 410 includes the plurality of belts and/or a plurality of straps 412 and 414. The plurality of belts and/or the plurality of straps 412 and 414 may further be provided with one or more of a loops and hooks fastening arrangement (also known as "Velcro®"), a buckle pin and holes fastening arrangement, and a spring-loaded friction buckle fastening arrangement.

On tightening the fastening arrangement 410, the one or more liner pads 210 and 212 grasp the skin of the portion 802. When a user walks, runs, jumps, etc. the reactionary force applied by the ground is transferred through the foot locating member 202 (or the wearable shoe 602), the one or more bracing members 206 and 208, and the one or more liner pads 210 and 212, to a great extent, to gastrocnemius (calf), soleus, and anterior tibialis muscles (See FIG. 1B) and possibly to some extent, in some embodiments with extended lengths of the one or more bracing members 206 and 208, to the patellar tendon (See FIG. 1C). Therefore, only a partial or no amount of force is applied to the ankle joint (See FIGS. 1A and 1B).

Example 1

Figure 9:
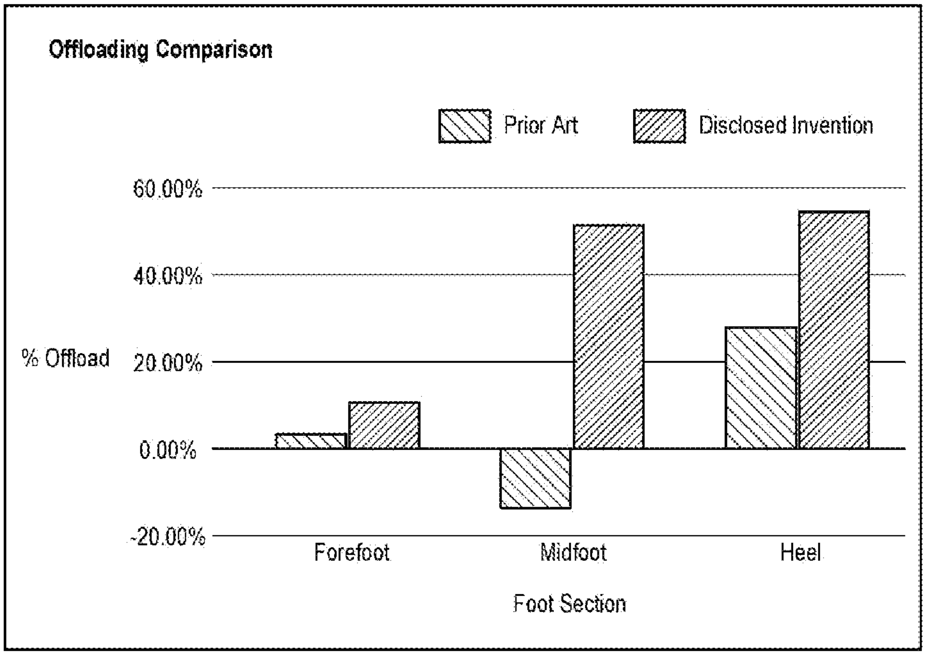
FIG. 9 illustrates experimental results of a comparison study performed between the present invention and prior art offloading devices.

FIG. 9 illustrates experimental results 900 of a comparison study performed between the present invention and prior art offloading devices. FIG. 9 on Y-axis shows percentage of body weight offloaded vis-à-vis on X-axis several different regions of the foot (viz. forefoot, midfoot, and heel). Tests were performed using a pressure-sensing insole while a user wore the respective devices with a wearable shoe on top of the respective devices. The results illustrate offloads of up to 55% (75 lb.) of body weight from the heel and the midfoot section during normal walking gait. This is an important comparison to the prior art offloading devices that claim offloading via only compression, which offloads 28% or less for a smaller area of the foot. The higher offloads can be attributed to a combination of factors including, but not limited to, deformability of the one or more liner pads 210 and 212, relatively higher coefficients of friction of the contact material of the one or more liner pads 210 and 212, deformability of the insole member 204, etc. Moreover, the embodiments of the offloading device of the present invention do not limit flexion but reduce the load on the ankle, thus reducing the pain of flexion. Flexion is important for daily activities of living, and function, and can also maintain the joint longer.

Various modifications to these embodiments are apparent to those skilled in the art, from the description and the accompanying drawings. The principles associated with the various embodiments described herein may be applied to other embodiments. Therefore, the description is not intended to be limited to the embodiments shown along with the accompanying drawings but is to provide the broadest scope consistent with the principles and the novel and inventive features disclosed or suggested herein. Accordingly, the invention is anticipated to hold on to all other such alternatives, modifications, and variations that fall within the scope of the present invention and appended claims.

The invention claimed is:

1. An offloading device configured for offloading a load from an ankle joint of a user, the offloading device comprising:

a foot locating member configured to locate therewithin a foot of the user;

one or more bracing members pivotably coupled to a left side and a right side of the foot locating member, the one or more bracing members are made from a rigid material and configured to grasp a portion of a lower leg that is located above the ankle joint;

one or more liner pads provided on inner surfaces of the one or more bracing members, wherein the one or more liner pads are configured to make contact with skin of the user; and a fastening arrangement configured to fasten the one or more bracing members to the portion of the lower leg that is located above the ankle joint, an insole member fastened to the foot locating member, the insole member comprising an insole anterior portion and an insole posterior portion, wherein a predefined clearance is provided between the insole member and the foot locating member along an entire length of the foot locating member, wherein at least the insole posterior portion is configured to undergo deformation within a predetermined range;

wherein the one or more liner pads are made from a deformable material coated with a contact material, having a coefficient of friction sufficient to inhibit a relative sliding between the one or more liner pads and the skin of the user such that a plurality of ground reaction forces are transferred from the foot locating member through the one or more bracing members to the portion of the lower leg located above the ankle joint, and thereby reduce the load on the ankle joint.

2. The offloading device as claimed in claim 1, wherein the insole member comprises a padding portion, a right-side suspension portion, and a left-side suspension portion, and wherein the insole member is suspended from lateral surfaces of the foot locating member.

3. The offloading device as claimed in claim 2, wherein the foot locating member comprises a basal locating member made from a rigid material, a left-side arm member, and a right-side arm member, the left-side arm member and the right-side arm member coupled to the basal locating member, on a left and a right side of the basal locating member, respectively;

wherein the right-side suspension portion and the left-side suspension portion allow the insole member to be suspended from the right-side arm member and the left-side arm member respectively, to provide the predefined clearance between the insole member and the foot locating member along the entire length of the foot locating member.

4. The offloading device as claimed in claim 3, wherein the one or more bracing members are pivotably coupled to the foot locating member through first apertures provided in upper portions of the left-side arm member and the right-side arm member, respectively, the first apertures aligning with second apertures provided in lower portions of the one or more bracing members.

5. The offloading device as claimed in claim 1, wherein the foot locating member is embodied as a wearable shoe.

6. The offloading device as claimed in claim 5, wherein the one or more bracing members are pivotably coupled to the wearable shoe, through first apertures provided in upper portions of a left-side quarter portion and a right-side quarter portion of the wearable shoe, the first apertures aligning with second apertures provided in lower portions of the one or more bracing members.

7. The offloading device as claimed in claim 1, wherein the fastening arrangement comprises a plurality of belts and/or a plurality of straps.

8. The offloading device as claimed in claim 7, wherein the plurality of belts and/or the plurality of straps are provided with one or more of a loops and hooks fastening arrangement, a buckle pin and holes fastening arrangement, and a spring-loaded friction buckle fastening arrangement.

9. The offloading device as claimed in claim 1, wherein the one or more bracing members and the foot locating member form a unitary structure, and the one or more bracing members are pivotably coupled to the foot locating member through flexure hinges at the left side and the right side of the foot locating member.

10. An offloading device configured for offloading a load from an ankle joint of a user, the offloading device comprising:

a foot locating member configured to locate therewithin a foot of the user;

one or more bracing members pivotably coupled to a left side and a right side of the foot locating member, the one or more bracing members configured to grasp a portion of a lower leg that is located above the ankle joint;

one or more liner pads provided on inner surfaces of the one or more bracing members, wherein the one or more liner pads are configured to make contact with skin of the user; and a fastening arrangement configured to fasten the one or more bracing members to the portion of the lower leg that is located above the ankle joint, wherein the foot locating member comprises a basal locating member made from a rigid material, a left-side arm member, and a right-side arm member, the left-side arm member and the right-side arm member coupled to the basal locating member, on a left and a right side of the basal locating member, respectively, and an insole member provided above an upper surface of the basal locating member, the insole member comprising an insole anterior portion and an insole posterior portion, wherein a predefined clearance is provided between the insole member and the basal locating member along an entire length of the basal locating member, wherein at least the insole posterior portion is configured to undergo deformation within a predetermined range;

wherein the one or more liner pads are made from a deformable material coated with a contact material, having a coefficient of friction sufficient to inhibit a relative sliding between the one or more liner pads and the skin of the user such that a plurality of ground reaction forces are transferred from the foot locating member through the one or more bracing members to the portion of the lower leg located above the ankle joint, and thereby reduce the load on the ankle joint.

11. The offloading device as claimed in claim 10, wherein the one or more bracing members are pivotably coupled to the foot locating member through first apertures provided in upper portions of the left-side arm member and the right-side arm member, respectively, the first apertures aligning with second apertures provided in lower portions of the one or more bracing members.

12. The offloading device as claimed in claim 10, wherein the insole member comprises a padding portion, a right-side suspension portion, and a left-side suspension portion, wherein the left-side suspension portion and the right-side suspension portion allow the insole member to be suspended from the left-side arm member and the right-side arm member to provide the predefined clearance between the insole member and the foot locating member along the entire length of the foot locating member.

13. The offloading device as claimed in claim 10, wherein the fastening arrangement comprises a plurality of belts and/or a plurality of straps.

14. An offloading device for supporting an ankle joint of a user, the offloading device comprising:

a foot locating member configured to locate therewithin a foot of the user;

an insole member fastened to the foot locating member, the insole member comprising an insole anterior portion and an insole posterior portion, wherein a predefined clearance is provided between the insole member and the foot locating member along an entire length of the foot locating member, wherein at least the insole posterior portion is configured to undergo deformation within a predetermined range;

one or more bracing members pivotably coupled to the foot locating member on a left side and a right side of the foot locating member, the one or more bracing members configured to grasp a portion of a lower leg that is located above the ankle joint; and a fastening arrangement configured to fasten the one or more bracing members with the portion of the lower leg that is located above the ankle joint, wherein the foot locating member is embodied as a wearable shoe.

15. The offloading device as claimed in claim 14, wherein the one or more bracing members are pivotably coupled to the wearable shoe, through first apertures provided in upper portions of a left-side quarter portion and a right-side quarter portion of the wearable shoe, respectively, the first apertures aligning with second apertures provided in lower portions of the one or more bracing members.

16. The offloading device as claimed in claim 14, further comprising one or more liner pads provided on inner surfaces of the one or more bracing members, wherein the one or more liner pads are configured to make contact with a skin of the user, wherein the one or more liner pads are made from a deformable material coated with a contact material.

* * * * *